United States Patent [19]

Tsuji

[11] Patent Number: 5,776,782
[45] Date of Patent: Jul. 7, 1998

[54] METHOD FOR MEASURING FLUORESCENCE RESONANCE ENERGY TRANSFER

[75] Inventor: Akihiko Tsuji, Hamamatsu, Japan

[73] Assignee: Hamamatsu Photonics K.K., Shizuoka-ken, Japan

[21] Appl. No.: 684,268

[22] Filed: Jul. 17, 1996

Related U.S. Application Data

[63] Continuation of Ser. No. 389,391, Feb. 16, 1995, abandoned.

[30] Foreign Application Priority Data

Feb. 16, 1994 [JP] Japan ................... 6-019500

[51] Int. Cl.$^6$ ................... G01N 21/62; G01N 21/64; G01N 33/00
[52] U.S. Cl. ................... 436/171; 436/164; 436/172; 436/805; 436/94; 422/82.07; 435/6; 424/9.6
[58] Field of Search ................... 436/172, 164, 436/171, 805, 94; 422/82.07; 424/9.6; 435/6

[56] References Cited

U.S. PATENT DOCUMENTS

| | | | |
|---|---|---|---|
| 4,822,746 | 4/1989 | Walt | 436/528 |
| 5,254,477 | 10/1993 | Walt | 436/172 |

FOREIGN PATENT DOCUMENTS

| | | | |
|---|---|---|---|
| 0070685 | 1/1983 | European Pat. Off. | G01N 33/58 |
| 0229943 | 7/1987 | European Pat. Off. | G01N 33/533 |

OTHER PUBLICATIONS

Tsien et al, "Fret for Studying Intracellular Signalling", Trends in Cell Biology, vol. 3, Jul. 1993, pp. 242–245.
Oida et al, "Fluorescense Lifetime Imaging Microscopy (Flimscopy)" Biophys. J, Biophysical Society, vol. 64, Mar. 1993, pp. 676–685.
Morrison, "Time-Resolved Detection of Energy Transfer: Theory and Application to Immunoassays", Analytical Biochemistry 174, 101–120 (1988).
Clegg et al, (1992), "Fluorescence resonance energy transfer analysis of the structure of the four-way DNA junction", Biochemistry 31:4846–4856.
Selvin, (1995), "Fluorescence resonance energy transfer", Meth. Enzymol. 246:300–334.
Clegg, (1995), "Fluorescence resonance energy transfer", Curr. Op. Biol. 6:103–110.
Zimet et al, (1995), "Calculation of resonance energy transfer in crowded biological membranes", Biophys. J. 68:1592–1603.
Lakowicz et al, (1991), "Correction for incomplete labeling in the measurement of distance distributions by frequency domain fluoremetry", Anal. Biochem. 195:243–254.
Parkhurst et al, (1995), "Kinetic studies by fluorescence resonance energy transfer employing a double labeled oligonucleotide: hydbridization to the oligonucleotide complement and to single stranded DNA", Biochem. 34(1):285–292.
Cardullo et al, (1988), "Detection of nucleic acid hybridization by nonradioactive fluorescence resonance energy transfer", Proc. Natl. Acad. Sci. 85:8790–8794.
Bottiroli et al, (1992), "Fluorescence resonance energy transfer imaging as a tool for in situ evaluation of cell morphofunctional characteristics" J. Photochem. Photobiol. B: Biol. 12:413–416.

*Primary Examiner*—Bradley L. Sisson
*Attorney, Agent, or Firm*—Sughrue, Mion, Zinn, Macpeak & Seas, PLLC

[57] ABSTRACT

A plurality of light emission molecules, having different light emission lifetimes, are irradiated with excitation light so that the light emission molecules emit light. The emitted light is divided into at least two different wavelength regions. Temporal changes in each of the at least two wavelength regions of the light emission is measured over at least two different time periods. Information on energy transfer generated between the plurality of light emission molecules is determined based on the measured results in each of the wavelength regions over each of the time periods.

26 Claims, 14 Drawing Sheets

FIG. 4
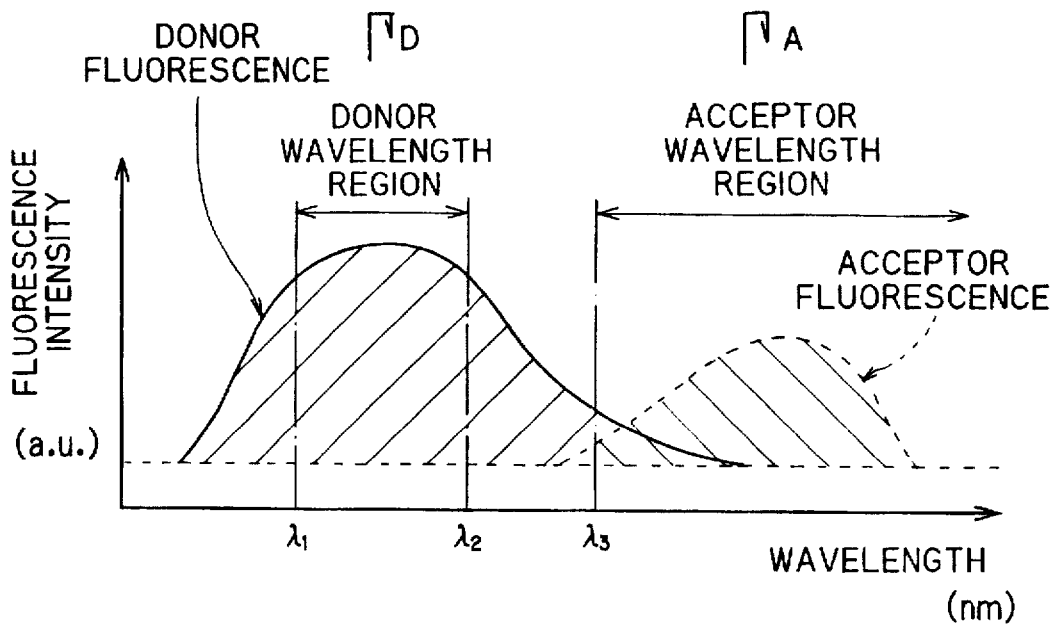
FIG. 5(a)
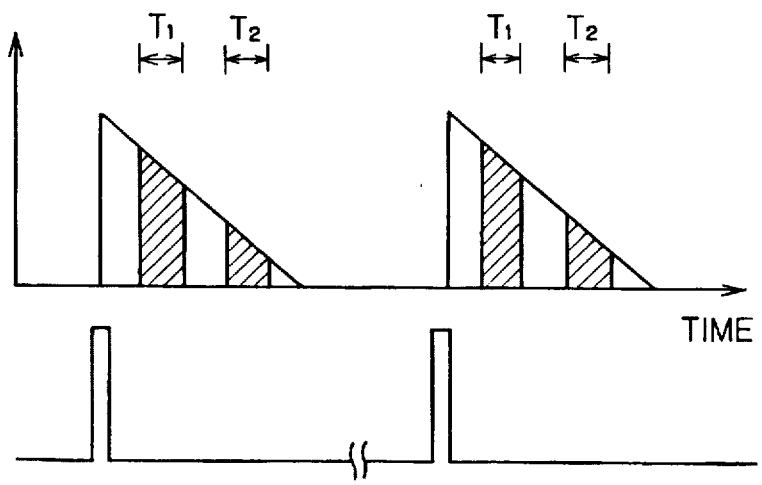
FIG. 5(b)
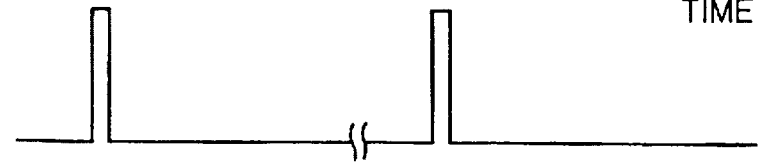
FIG. 5(c)
FIG. 5(d)
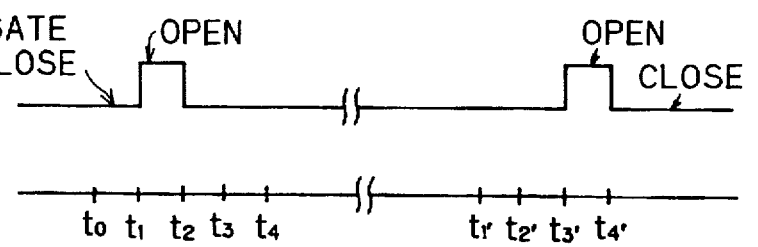

5-(2-((IODOACETYL)AMINO)ETHYL)AMINO)NAPHTHALENE-1-SULFONIC ACID
(1,5-IEA DANS)

TETRAMETHYLRHODAMINE-5-(AND-6)-ISOTHIOCYANATE (TRITC)

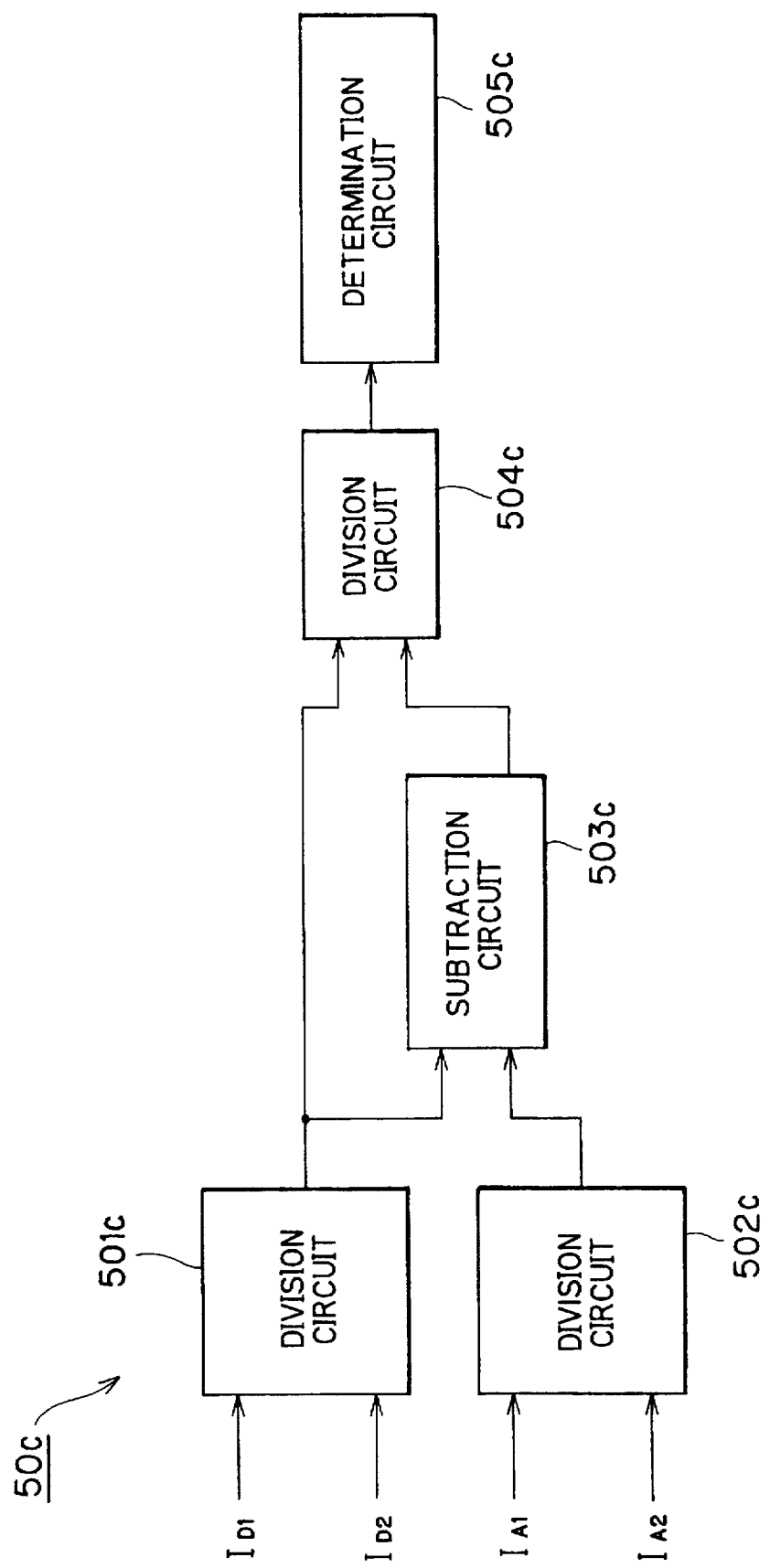

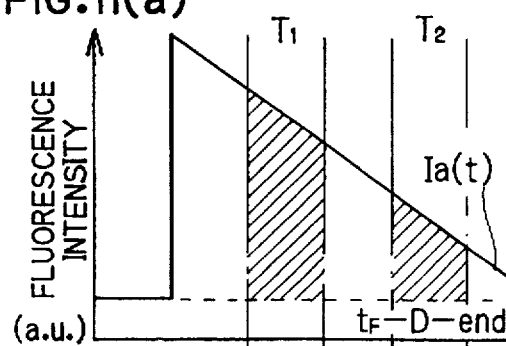
FIG.11(a)
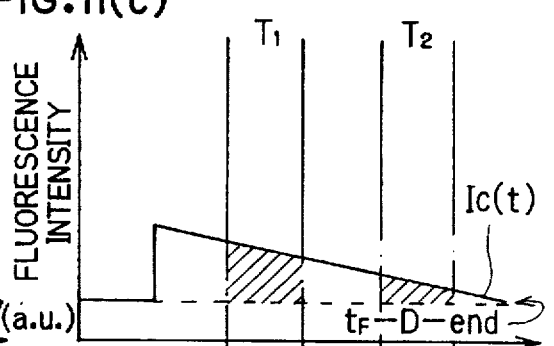
FIG.11(c)
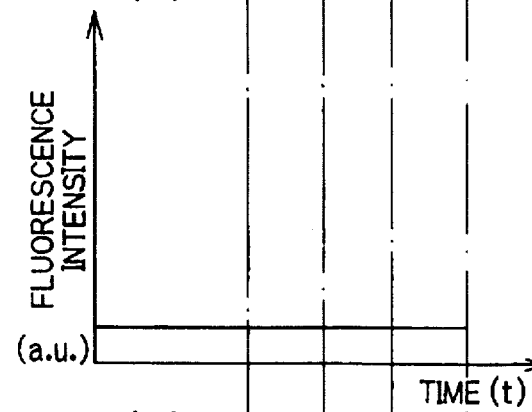
FIG.11(b)
FIG.11(d)
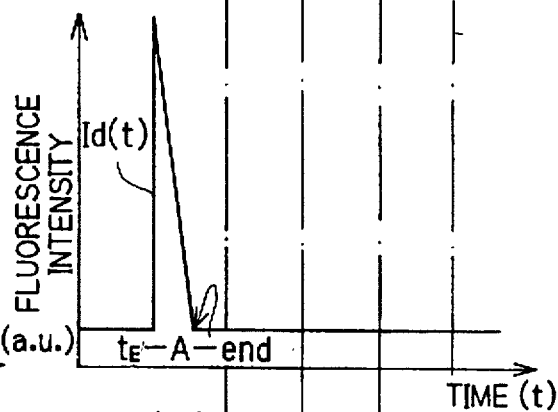
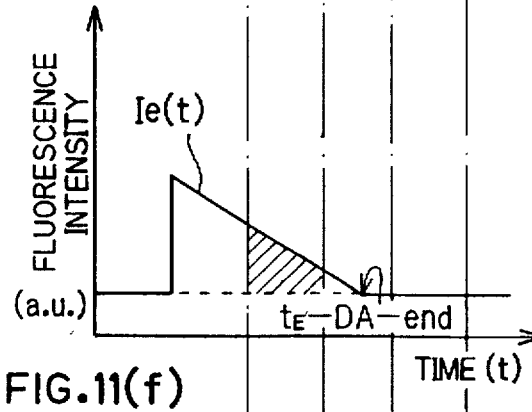
FIG.11(e)
FIG.11(g)
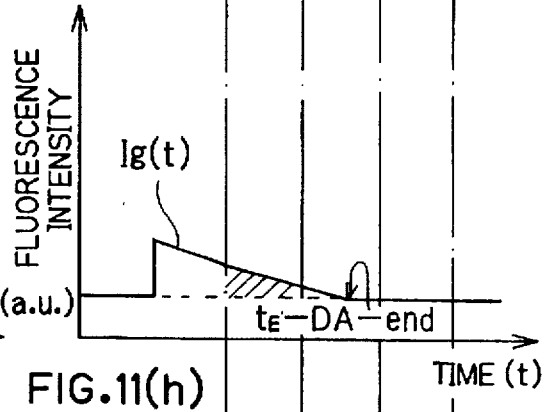
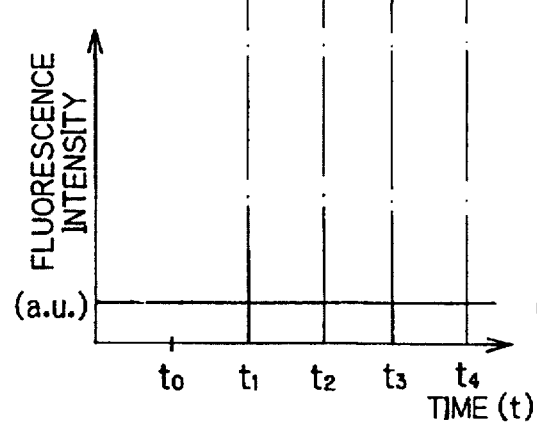
FIG.11(f)
FIG.11(h)
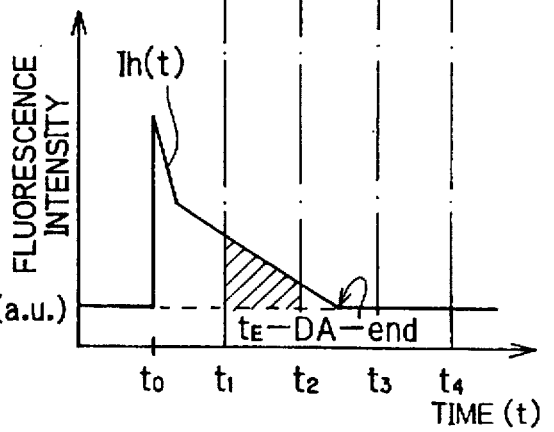

1

METHOD FOR MEASURING FLUORESCENCE RESONANCE ENERGY TRANSFER

This application is a continuation of U.S. Ser. No. 08/389,391, filed Feb. 16, 1995 now abandoned.

BACKGROUND OF THE INVENTION

1. Field of the Invention

The present invention relates to a method and an apparatus for identifying substances by measuring the energy transferred between and within molecules and more particularly to detecting small amounts of substances within living cells by measuring energy transfer.

2. Description of the Related Art

Fluorescence resonance energy transfer (FRET) within or between two different types of molecule, that occurs when energy from an excited donor fluorophore is transferred directly to an acceptor fluorophore, is a useful phenomenon for studying the character of molecules. This method is especially useful for in vitro measurements of small quantities of substances and can be applied to analysis of genetic information to measure expression of genes and changes in the primary structure of DNA and RNA to a high degree of precision.

Next, an explanation will be provided for a general method for measuring energy transfer from an excited fluorophore (donor) to an absorber (acceptor).

1. The spectra, including changes in the spectra, of fluorescence from the donor and acceptor are measured.

2. Reduction in intensity of fluorescence from the donor or increase in intensity of fluorescence from the acceptor is measured.

3. The speed at which the intensity of the fluorescent intensity of the donor decreases after pulse-laser excitation (i.e., the fluorescence lifetime) is measured.

However, sometimes the sample contains numerically more molecules that do not emit energy (i.e., free molecules) than molecules that do emit energy, in which case measurement using this three-step method is impossible. This three-step method is also not possible when the density of energy-transferring donors or acceptors can not be determined. Because in this three-step method fluorescence from both energy-emitting and non-energy emitting molecules is measured, the characteristic change in fluorescence which occurs from energy transfer is buried in the fluorescence produced by molecules that do not emit energy. Also, when the increase in fluorescence intensity in the acceptor is measured in step 2, the acceptor directly absorbs some of the excitation light and fluoresces at an intensity significant compared to the intensity of acceptor fluorophore emission from energy transfer. This makes determination of only the energy transfer induced fluorescence from the acceptor fluorophore impossible.

Larry E. Morrison describes a method of measuring energy transfer under these conditions (Analytical Biochemistry 174, pp 101–120, 1988). His technique "requires the selection of donor and acceptor fluorophores such that the fluorescence lifetime of the donor is greater than the fluorescence lifetime of the acceptor." The fluorescence emitted from the acceptor is measured a predetermined duration of time (set by a delay gate) after the donor fluorophore has been excited by the pulse of light. With this method, the fluorescence emitted from the acceptor as a result of direct absorption of the excitation light is temporally separated from the fluorescence emitted from the acceptor by energy transfer. Measurement of energy transfer is improved because the fluorescence contributed by light excitation (i.e., not by energy transfer) of the acceptor is eliminated.

Roger Y. Tsein et al. describe a method wherein the ratio of the fluorescent intensities of the donor and the acceptor when excited by a certain wavelength excitation light is calculated and an image produced from the results (Trends in Cell Biology, Vol. 3, pp. 242–245, 1993). Takatoku Oida et al. describe temporal analysis of imaging (Biophys. J., Vol. 64, pp. 676–685, 1993). With these two methods, fluorescence for each fluorophore can be separated by electric gating of detector signals. Scattering of light or mixing with light other than the objective fluorescence can be prevented. Precision in measuring fluorescent intensity can be increased by differences in the length of the optical pathways. Influence of unknown densities of molecules can also be reduced. Energy transfer within cultivated cells can be measured under a microscope.

SUMMARY OF THE INVENTION

However, when the amount of free donor fluorophores that do not emit energy becomes rather large, the long wavelength region of the donor fluorescence gets largely mixed in the short wavelength region of the acceptor fluorescence, with the result that the fluorescence from the donor and from the acceptor can not be separated. For these reasons, energy transfer in living samples, such as cultivated cells, is particularly difficult to measure.

It is an objective of the present invention to provide a method and an apparatus that allow measurement of energy transfer that occurs in only a few molecules even when energy transfer does not occur in most of the molecules.

In order to attain the above object and other objects, the present invention provides a method of measuring energy transfer between a plurality of light emission molecules, the method comprising the steps of: irradiating with excitation light a plurality of light emission molecules, having different light emission lifetimes, so that the light emission molecules emit light; dividing the emitted light into at least two different wavelength regions; measuring temporal changes in each of the at least two wavelength regions of the light emission over at least two different time periods; and determining information on energy transfer generated between the plurality of light emission molecules based on the measured results in each of the wavelength regions over each of the time periods.

The plurality of light emission molecules may include two kinds of fluorophores having different fluorescence lifetimes.

The wavelength dividing step may divide the emitted fluorescence into a first wavelength region and a second wavelength region different from each other. The temporal change measuring step may measure temporal changes in the first wavelength region and the second wavelength region of the fluorescence over a first time period and a second time period different from each other. The energy transfer information determining step may determine the information, based on the fluorescence in each of the first and second wavelength regions over each of the first and second time periods.

Fluorescence intensity of fluorescence from the acceptor fluorophores attenuates over time after the irradiation of the excitation light, in accordance with its fluorescent lifetime, the attenuation being substantially completed at a first timing. Fluorescence intensity of fluorescence from the donor fluorophores attenuates over time after the irradiation of the excitation light, in accordance with its fluorescent lifetime, the attenuation being substantially completed at a second timing. The fluorescence lifetime of the donor fluorophores varies when energy transfer occurs from the donor fluorophores to the acceptor fluorophores so that fluorescence intensity of fluorescence from the donor fluorophores attenuates over time when the energy transfer occurs after the irradiation of the excitation light, in accordance with its varied fluorescent lifetime, the attenuation being substantially completed at a third timing different from the second timing. The temporal change measuring step may include the step of setting the first time period between the first timing and the third timing and setting the second time period between the third timing and the second timing.

The energy transfer information determining step may calculate the following formula with the fluorescence over each time period:

$$\{(I_{D2}/I_{D1})-(I_{A2}/I_{A1})\}/(I_{D2}/I_{D1})$$

wherein $I_{D1}$ is the intensity of fluorescence in the first wavelength region obtained over the first time period; $I_{D2}$ is the intensity of fluorescence in the first wavelength region obtained over the second time period; $I_{A1}$ is the intensity of fluorescence in the second wavelength region obtained over the first time period; and $I_{A2}$ is the intensity of fluorescence in the second wavelength region obtained over the second time period.

According to another aspect, the present invention provides a device for measuring energy transfer between a plurality of light emission molecules, the device comprising: a light source for irradiating a plurality of light emission molecules having different light emission lifetimes with excitation light so that the plurality of light emission molecules emit light; a wavelength divider for dividing the emitted light into a first wavelength region and a second wavelength region different from each other; a measuring unit for measuring temporal changes in the light in the first wavelength region and the second wavelength region over a first time period and a second time period different from each other; and a determination unit for determining information on energy transfer occurring between the light emission molecules, based on the light intensity of the first and second wavelength regions during the first time period and the second time period.

BRIEF DESCRIPTION OF THE DRAWINGS

The above and other objects, features and advantages of the invention will become more apparent from reading the following description of the preferred embodiment taken in connection with the accompanying drawings in which:

FIG. 4 illustrates how the wavelength regions are set for the fluorescence light from donor and acceptor;

FIG. 5(a) shows temporal change in intensity of fluorescence from fluorophore;

FIG. 5(b) shows an excitation light irradiation timing for causing the fluorophore to emit fluorescence shown in FIG. 5(a);

FIG. 5(c) shows a gate opening timing according to a first method;

FIG. 5(d) shows a gate opening timing according to a second method;

FIG. 10 is a circuitry diagram of an example of the calculation device for calculating the parameter Z;

FIG. 11(a) shows temporal change in intensity of fluorescence at wavelength region $\Gamma_D$ from free donor fluorophore;

FIG. 11(b) shows temporal change in intensity of fluorescence at wavelength region $\Gamma_D$ from free acceptor fluorophore;

FIG. 11(c) shows temporal change in intensity of fluorescence at wavelength region $\Gamma_A$ from free donor fluorophore;

FIG. 11(d) shows temporal change in intensity of fluorescence at wavelength region $\Gamma_A$ from free acceptor fluorophore;

FIG. 11(e) shows temporal change in intensity of fluorescence at wavelength region $\Gamma_D$ from donor fluorophore when energy transfer occurs;

FIG. 11(f) shows temporal change in intensity of fluorescence at wavelength region $\Gamma_D$ from acceptor fluorophore when energy transfer occurs;

FIG. 11(g) shows temporal change in intensity of fluorescence at wavelength region $\Gamma_A$ from donor fluorophore when energy transfer occurs;

FIG. 11(h) shows temporal change in intensity of fluorescence at wavelength region $\Gamma_A$ from acceptor fluorophore when energy transfer occurs;

DETAILED DESCRIPTION OF THE PREFERRED EMBODIMENT

Figure 1:
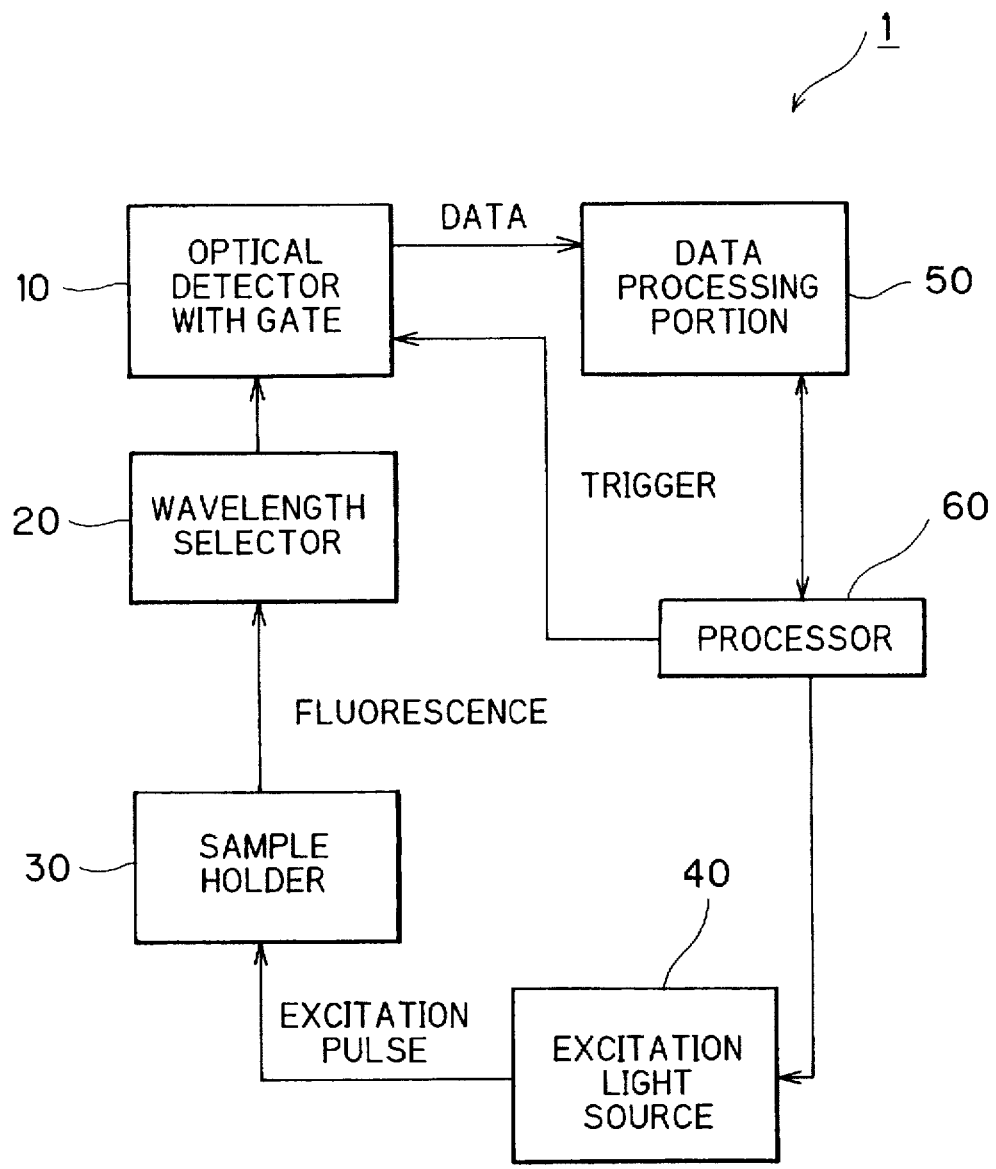
FIG. 1 shows a schematic structure of the energy transfer measuring device of an embodiment of the present invention.

A method and instrument for measuring fluorescence resonance energy transfer according to a preferred embodiment of the present invention will be described while referring to the accompanying drawings wherein like parts and components are designated by the same reference numerals to avoid duplicating description.

As shown in FIG. 1, an energy-transfer measuring instrument 1 according to the present invention includes: an excitation light source 40; a sample holder 30; a wavelength divider 20 such as a filter, a prism, or a diffraction grating; a light detector 10 including a gate; a data processing portion 50; and a processor 60.

The excitation light source 40 is for irradiating a sample mounted in the sample holder 30 with excitation light. The excitation light source 40 can be a gas laser such as a nitrogen, helium-neon, or argon ion laser, a semiconductor laser, or an ultraviolet light source. The laser is preferable for the light source, and the gas laser is more preferable because laser light, preferably generated by a gas laser, makes a good excitation light in terms of excitation ability and in terms of intensity. The light detector 10 can be a photomultiplier tube, a photodiode, an avalanche photodiode, a streak tube, or a charge-coupled device (CCD).

FRET is generated from resonant interaction between two molecules: an energy contributing donor molecule and an energy receiving acceptor. Both the donor molecule and the acceptor molecule are light emission molecules, such as fluorescent, phosphorescent, and chemiluminescent molecules, which emit light when excited by excitation light. The donor molecule and the acceptor molecule show different emission lifetimes. Energy transfer can occur when the emission spectrum of the donor overlaps the absorption spectrum of the acceptor. Also, the donor and the acceptor must be within a certain distance (for example, less than 8 nm) from each other. Preferable donor/acceptor combinations that can be used with this method are fluorescent donors with fluorescent or phosphorescent acceptors, or phosphorescent donors with phosphorescent or fluorescent acceptors.

The measurement device of the present invention will be described below, with reference to an example wherein the sample to be measured includes two fluorophores that show different fluorescence lifetimes when excited by the excitation light.

Fluorescence generated upon irradiation with an excitation light can be separated into a predetermined number (two in the present embodiment) of different wavelengths by using the wavelength divider 20. Afterward, the divided light is measured by the light detector 10. Measurement by the light detector 10 is performed after a predetermined duration of time passes after irradiation by the excitation light source 40. That is, when irradiation is performed using a pulse of light from the excitation light source 40, the light detector 10 is triggered into operation after the lowering edge of the pulse of light. The temporal attenuation of the detection signal from the light detector 10 is read over at least two separate time periods and sent to the data processing portion 50. Detection signals can be read over two different time periods by opening the gate of the light detector 10 during the time periods. The processor 60 controls drive of the excitation light source 40 and the light detector 10 and processes of the data processing portion 50.

However, the light detector 10 need not be provided with gates. For example, the light detector 10 could constantly output detection signals to the data processing portion 50 and the processing portion 50 operated to separate the detection signals by time periods. However, the excitation light irradiating timing and the two detection signal pick up durations should be set within a very short time period relative to the response speed of the data processing portion 50. Accordingly, it is desirable to set the two time periods directly by the light detector 10.

The combination of the wavelength divider 20 and the light detector 10 serves to divide light emitted from the excited sample into two separate wavelengths and into two separate time periods so as to obtain data on four separate physical values. The data can then be processed by the data processing portion 50 in a manner to be described later to determine the existence of energy transfer, the condition of energy transfer, and the other information.

Figure 2:
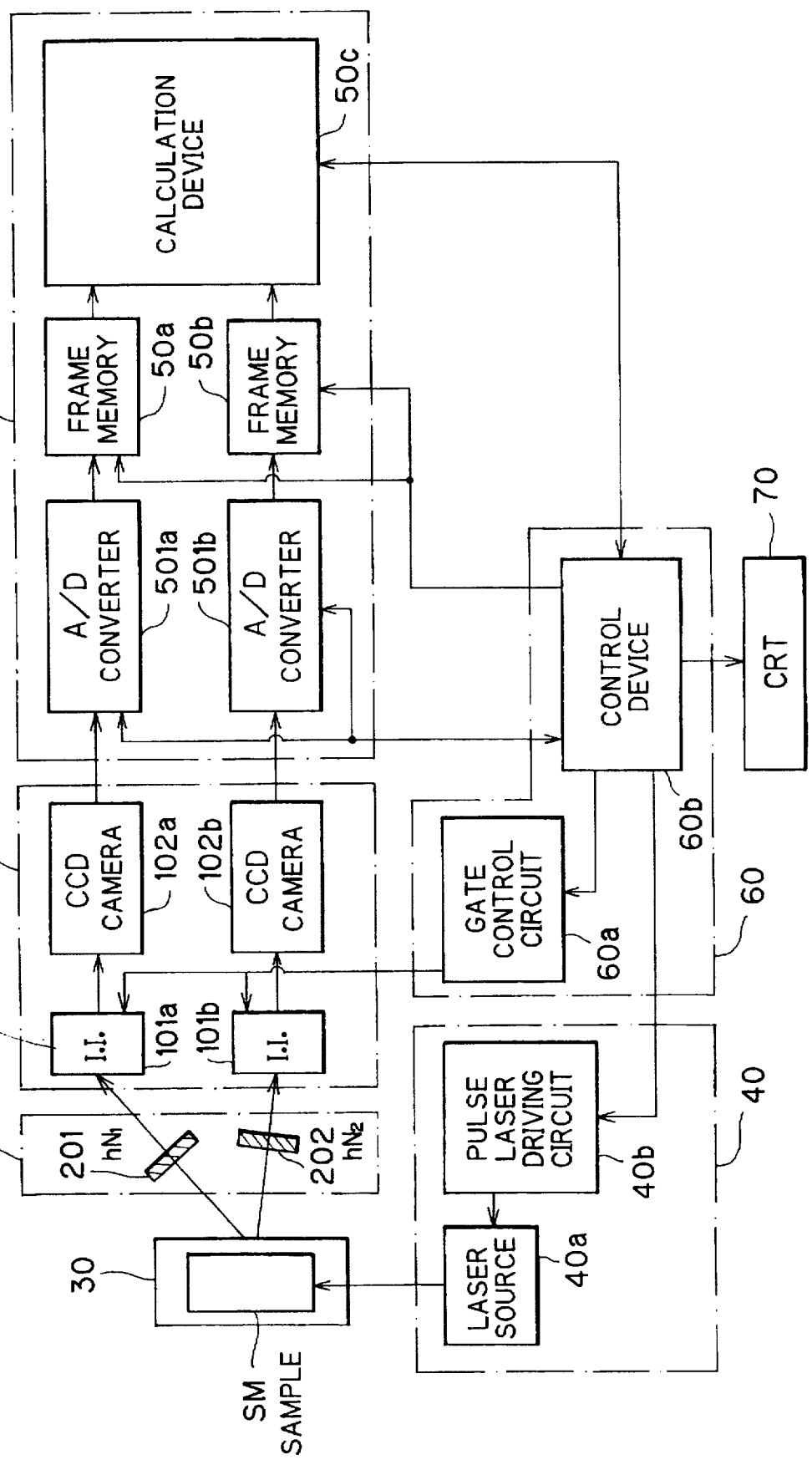
FIG. 2 shows a structure of a detailed example of the energy transfer measuring device of the embodiment.

FIG. 2 shows a more detailed example of the energy transfer measurement instrument 1 shown in FIG. 1. The sample SM mounted in the sample holder 30 in this example contains donor and acceptor fluorophores. The light source 40 includes a gas laser 40a and a pulse laser drive circuit 40a, which is for driving the gas laser 40a in pulses. The sample SM will emit fluorescence upon irradiation by light from the gas laser 40a. Because the sample includes fluorescent molecules of both the donor and the acceptor, the wavelengths of fluorescence from the sample span a wavelength region $\Gamma_D$ of light emitted from the excited donor and a wavelength region $\Gamma_A$ of light emitted from the acceptor. A transmission filter 201, with a transmission region corresponding to the wavelength region $\Gamma_D$, and a transmission filter 202, with a transmission region corresponding to the wavelength region $\Gamma_A$, serve as the wavelength divider 20. The generated fluorescence is therefore divided into two different wavelength regions when passed through these filters 210 and 202.

Fluorescence at the wavelength regions $\Gamma_D$ and $\Gamma_A$ are inputted to image intensifiers 101a and 101b respectively. Each of the image intensifiers 101a and 101b is one type of photomultiplier tube for converting the energy of the inputted light into electrons while maintaining the planar or spatial distribution (i.e., image) of the light. Each image intensifier includes a photocathode and a multichannel plate (MCP). The excitation-induced fluorescence is incident on the photocathode and converted into electrons. Electrons are then multiplied in the MCP. The MCP functions a gate for multiplying these electrons only when applied with a driving voltage. The multiplied electrons are irradiated on a fluorescent substance placed at the output surface of the image intensifier, where they are converted into fluorescence (i.e., a fluorescent image).

The fluorescent images thus outputted from the image intensifiers 101a and 101b are picked up by CCD cameras 102a and 102b respectively. The CCD cameras 102a and 102b are both precooled to a temperature of $-40°$ C. After the gas laser 40a outputs a pulse of excitation light, the gate control circuit 60a outputs a trigger signal simultaneously to both of the image intensifiers 101a and 101b. The image intensifiers 101a and 101b output signals (i.e., fluorescent images) only for the predetermined duration of time that they are inputted with trigger signals. The trigger signals are set so that the image intensifiers 101a and 101b output over a first time period $T_1$ and a second time period $T_2$ before the fluorescence attenuation of the sample completes. The CCD cameras 102a and 102b obtain images representing intensity of fluorescence emitted over the two time periods.

The fluorescence intensity of each pixel of the CCD cameras 102a and 102b integrated over each time period will be referred to as pixel fluorescence intensity hereinafter. The spatially-integrated value of the pixel fluorescence intensities of all the pixels of each CCD camera will be referred to as total fluorescence intensity.

The signal charges outputted from the CCD cameras 102a and 102b during the first time period $T_1$ and the second time period $T_2$ are successively converted to digital signals by the A/D converters 501a and 501b and accumulated in the frame memories 50a and 50b respectively. As a result, the pixel fluorescence intensities during the time periods $T_1$ and $T_2$ are obtained at wavelength regions $\Gamma_D$ and $\Gamma_A$ in the frame memories 50a and 50b respectively. The calculation device 50c then calculates total fluorescence intensity for each wavelength region by spatially integrating the pixel fluorescence intensities at each time period. The total fluorescence intensity at wavelength region $\Gamma_D$ over the first time period $T_1$ will be referred to as fluorescence intensity $I_{D1}$ hereinafter. The total fluorescence intensity at wavelength region $\Gamma_D$ over the second time period $T_2$ will be referred to as fluorescence intensity $I_{D2}$ hereinafter. The total fluorescence intensity at wavelength region $\Gamma_A$ over the first time period $T_1$ will be referred to as fluorescence intensity $I_{A1}$ hereinafter. The total fluorescence intensity at wavelength region $\Gamma_A$ over the second time period $T_2$ will be referred to as fluorescence intensity $I_{A2}$ hereinafter. Information on energy transfer can be calculated based on the fluorescence intensities $I_{D1}$, $I_{D2}$, $I_{A1}$, and $I_{A2}$, as will be described later. The fluorescence intensities and the calculated information on energy transfer are sent to the control device 60b so that it can be outputted to the CRT 70, which serves as an external output device.

Figure 3:
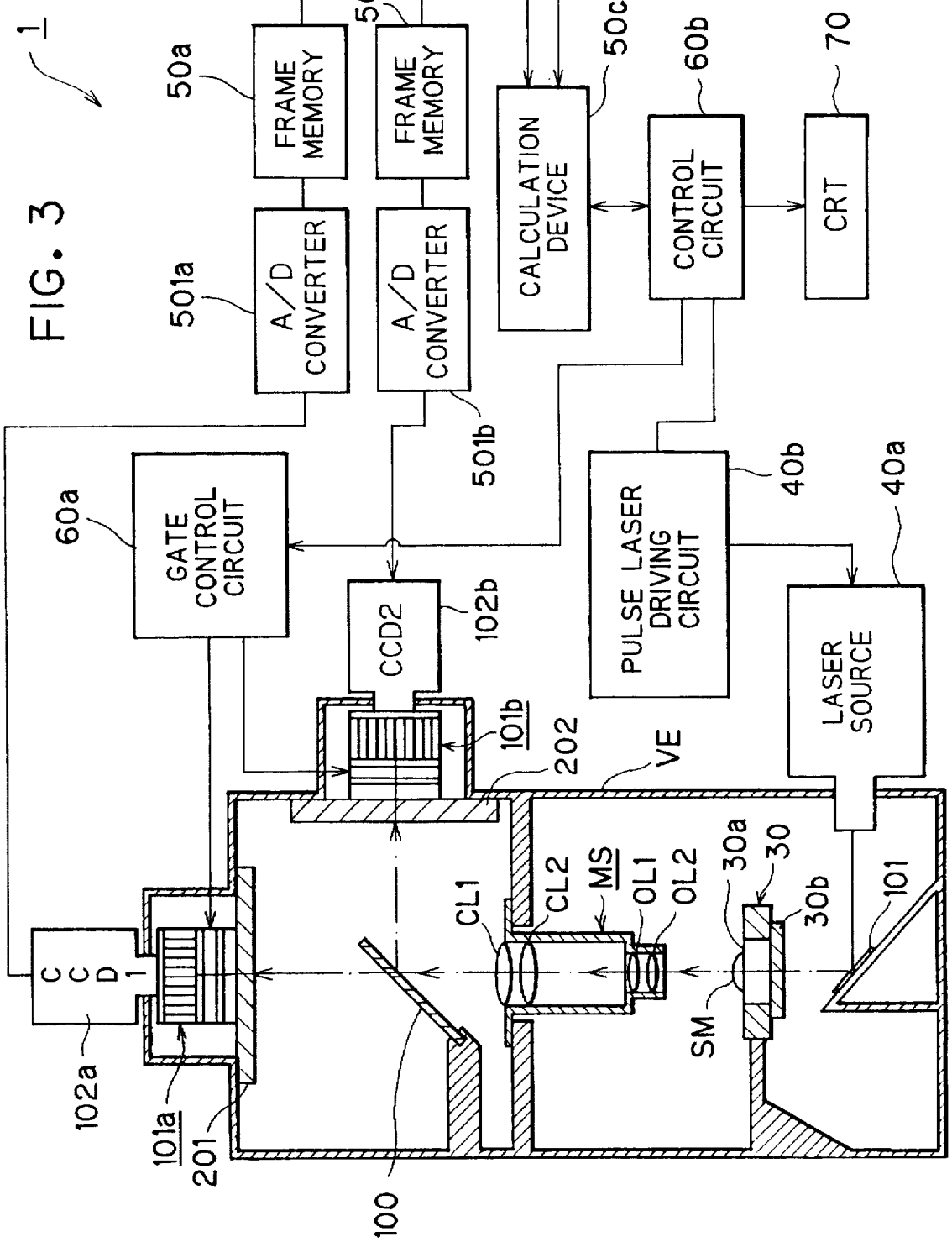
FIG. 3 shows a structure of a concrete example of the energy transfer measuring device of the embodiment.

FIG. 3 shows a concrete example of the device 1 shown in FIG. 2. Coherent excitation light emitted from the gas laser 40a reflects off a planar mirror 101, passes through an excitation transmission filter 30b and a sample mounting glass 30a and irradiates the sample SM mounted on the glass 30a. The fluorescence emitted from the sample SM is focused by a microscope MS so as to be incident on a half mirror 100. The half mirror 100 divides the incident light into two parts. One part passes through the half mirror 100 so as to be incident on the transmission filter 201 for the donor wavelength region $\Gamma_D$. The other part reflects off the half mirror 100 so as to be incident on the transmission filter 202 for the acceptor wavelength region $\Gamma_A$. The same processes described while referring to the device shown in FIG. 2 are performed on the fluorescence that passes through the transmission filters 201 and 202, whereupon the resultant fluorescence intensities and energy transfer information are displayed on the CRT 70.

The excitation light transmission filter 30b is for allowing transmission of excitation light at the wavelength region necessary for excitation of the donor and for blocking transmission of background light. The microscope MS includes objective lenses OL1 and OL2, positioned on the sample side of the microscope, and eyepiece lenses CL1 and CL2, positioned at the filter (i.e., 201 and 202) side of the microscope.

The energy transfer measurement device is housed in a light-blocking case VE for preventing external light from becoming incident on the sample, the CCD cameras 102a and 102b, and the like. This allows detection of energy transfer with greater precision.

Below will be given an explanation of a method for determining the donor wavelength region $\Gamma_D$ and the acceptor wavelength region $\Gamma_A$ at which the transmission filters 201 and 202 divide the fluorescence.

The graph shown in FIG. 4 indicates the spectral characteristics (i.e., relationship between wavelength and intensity) of fluorescence emitted from fluorescent molecules. The solid line represents changes in fluorescence from the donor and the dotted line represents changes in fluorescence from the acceptor. The donor wavelength region $\Gamma_D$ is defined to extend from wavelength $\lambda_1$ to wavelength $\lambda_2$ and the acceptor wavelength region $\Gamma_A$ is defined to extend from wavelength $\lambda_3$ on up. The wavelength $\lambda_2$ of the donor wavelength region $\Gamma_D$ is set below the rising edge of the acceptor fluorescence spectrum. Wavelength $\lambda_3$ is set so that five percent of the long wavelength part of the donor fluorescence is mixed in the acceptor wavelength region $\Gamma_A$. Because the spectral characteristics of respective kinds of fluorophores are known, the values $\lambda_1$, $\lambda_2$, and $\lambda_3$ (i.e., $\Gamma_D$ and $\Gamma_A$) can be determined for the respective fluorophores.

Below will be given an explanation of a method for determining timing of gate openings by the image intensifiers 101a and 101b, i.e., for determining the time periods T1 and T2.

Assume that the sample includes some free fluorophores (for example, free donor) having a specific fluorescence lifetime $\tau_F$. When the control device 60b shown in either FIG. 2 or 3 inputs the clock pulse shown in FIG. 5(b) to the pulse laser drive circuit 40b, the excited fluorophores in the sample SM emits fluorescence at intensities that attenuate over time as shown in FIG. 5(a).

The fluorescence intensity of the fluorescence over the first time period $T_1$ and over the second time period $T_2$ are obtained by applying a voltage to the MCP's of the image intensifiers 101a and 101b during the two time periods $T_1$ and $T_2$ after each pulse of excitation light shown in FIG. 5(b). The timing of this operation is shown in FIG. 5(c), and will be referred to as gate method A.

To improve the signal-to-noise ratio of the CCD cameras 102a and 102b, the light images outputted from the image intensifiers 101a and 101b can be picked up while driving the CCD cameras 102a and 102b in a slow scan. However, this lengthens the time required for the CCD cameras 102a and 102b to scan one frame. Therefore it is desirable to, as shown in FIG. 5(d), apply voltage to the MCP's of the image intensifiers 101a and 101b during one of the time periods (the first time period $T_1$ in this example) after the first pulse of excitation light. Then, after the second pulse of excitation light, voltage is applied to the MCP's of the image intensifiers 101a and 101b during the other time period (the second time period $T_2$ in this example). This will be referred to as gate method B.

The signal-to-noise ratio can be further improved by repeatedly sampling the pixel fluorescence intensity during the predetermined time periods T1 and T2 using either gate method A or B and accumulating the pixel fluorescence to obtain the total fluorescence intensity.

Concrete values of the first time period $T_1$ and the second time period $T_2$ should be set according to the fluorescence lifetime $\tau$ of the fluorophores to be measured by the energy transfer detector 1.

Figure 6A:
FIG. 6(a) shows chemical formulas of IEADANS.
Figure 6B:
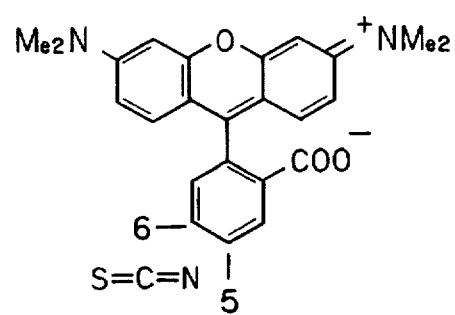
FIG. 6(b) shows chemical formulas of TRITC.

Below will be described a method for determining the values T1 and T2 with reference to an example for using IEADANS (shown in FIG. 6(a)) as donor and TRITC (shown in FIG. 6(b)) as acceptor. It is known that IEADANS (donor) has a fluorescence lifetime $\tau_{F-D}$ of 15.0 ns under circumstances where no TRITC (acceptor) is present close to IEADANS, that is, when IEADANS is free. It is also known that TRITC has a fluorescence lifetime $\tau_{F-A}$ of 1.5 ns when free, that is, under circumstances where no IEADANS is present close to TRITC. Because the fluorescence lifetime of IEADANS (donor) is longer than that of TRITC (acceptor), they are suitable for being measured by the device of the present invention.

Figure 7A:
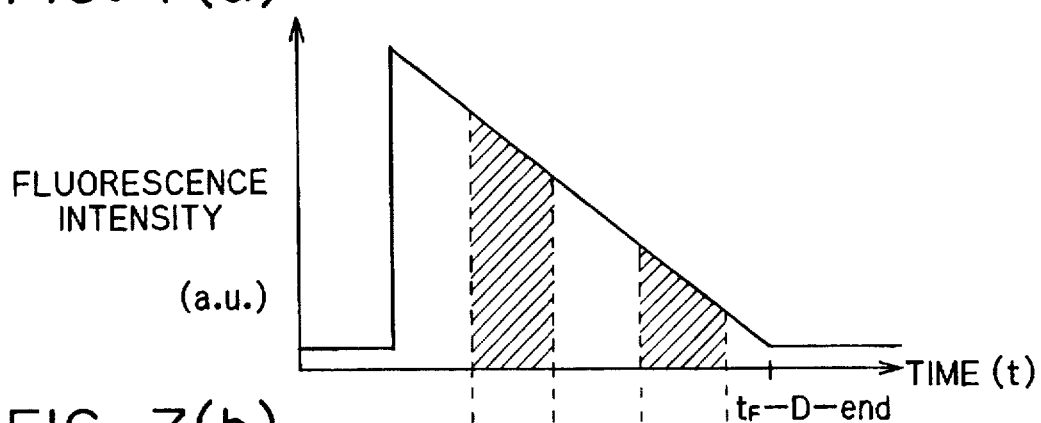
FIG. 7(a) shows temporal change in intensity of fluorescence from free donor fluorophore.
Figure 7B:
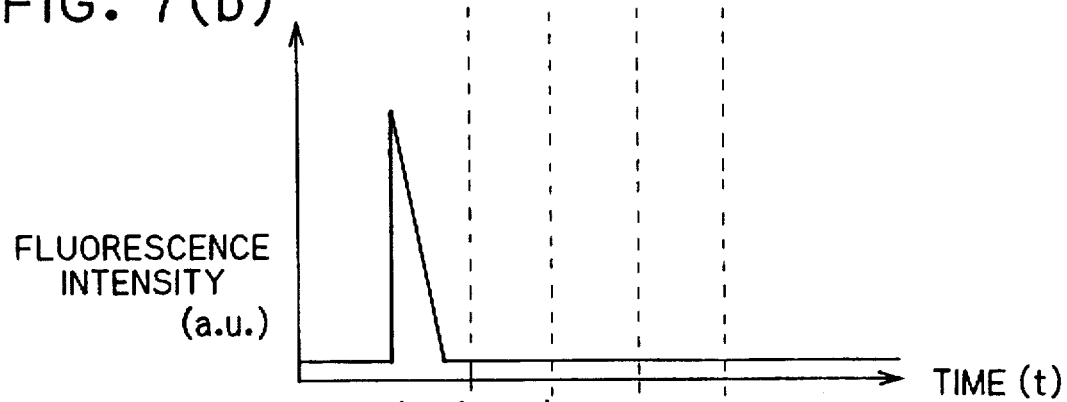
FIG. 7(b) shows temporal change in intensity of fluorescence from free acceptor fluorophore.
Figure 7C:
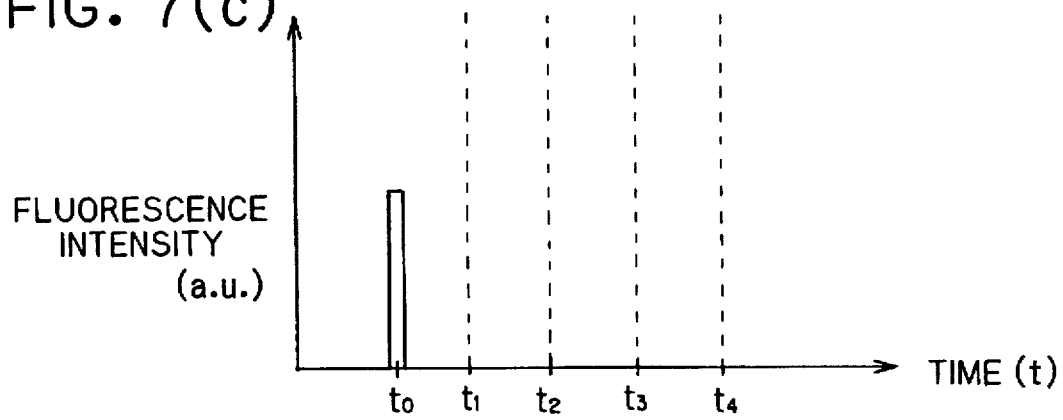
FIG. 7(c) shows an excitation light irradiation timing for causing the free donor fluorophore to emit fluorescence shown in FIG. 7(a) and for causing the free acceptor fluorophore to emit fluorescence shown in FIG. 7(b)

The first time period $T_1$ and the second time period $T_2$ should be set as shown in FIG. 7 when the sample includes these free donor and free acceptor molecules. It is noted that values along the vertical axis of FIG. 7 are logarithmically expressed. When this sample is irradiated with the pulse of excitation light shown in FIG. 7(c), the free donor emits fluorescence over time as shown in FIG. 7(a) and the free acceptor emits fluorescence over time as shown in FIG. 7(b). As can be seen in FIGS. 7(a) and 7(b), fluorescence from both the free donor and the free acceptor attenuates with passage of time until the fluorescence from the free acceptor attains an intensity of zero at time point $t_{F-A-end}$ and the fluorescence from the free donor attains an intensity of zero at time point $t_{F-D-end}$. The first time period $T_1$ is set to begin after time point $t_{F-A-end}$ and the second time period $T_2$ is set to begin after first time period $T_1$ and to end before the time point $t_{F-D-end}$.

Figure 8:
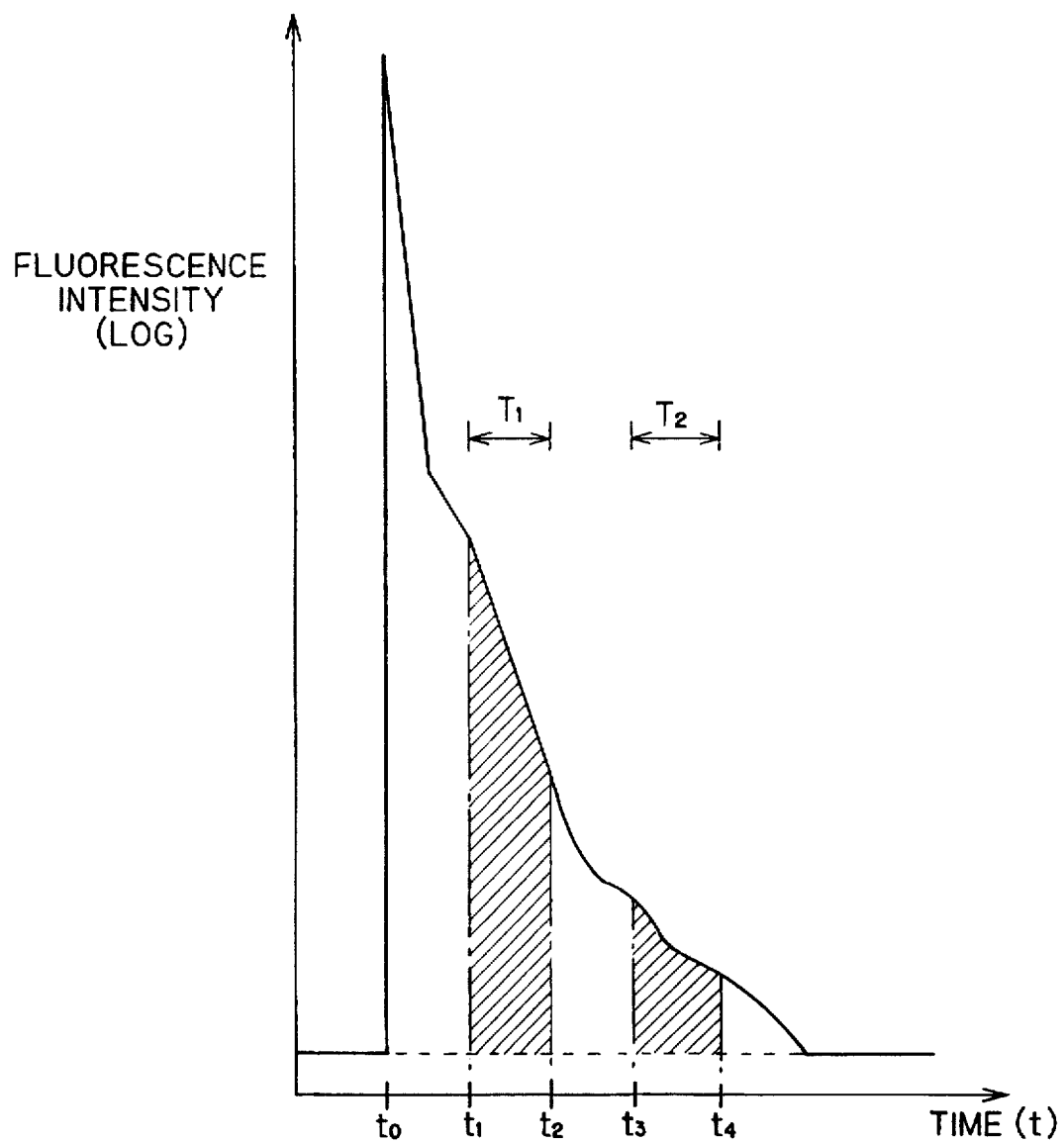
FIG. 8 shows temporal change in intensity of fluorescence from a sample containing free donor fluorophores and free acceptor fluorophores.
Figure 9A:
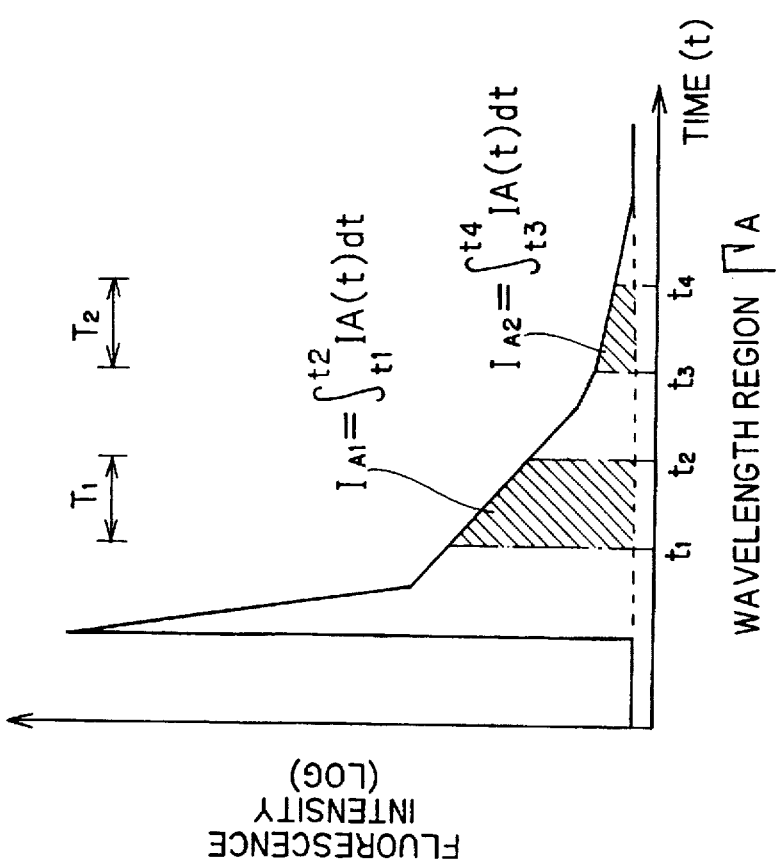
FIG. 9(a) shows temporal change in intensity of fluorescence of wavelength region $\Gamma_D$ of the fluorescence of FIG. 8.
Figure 9B:
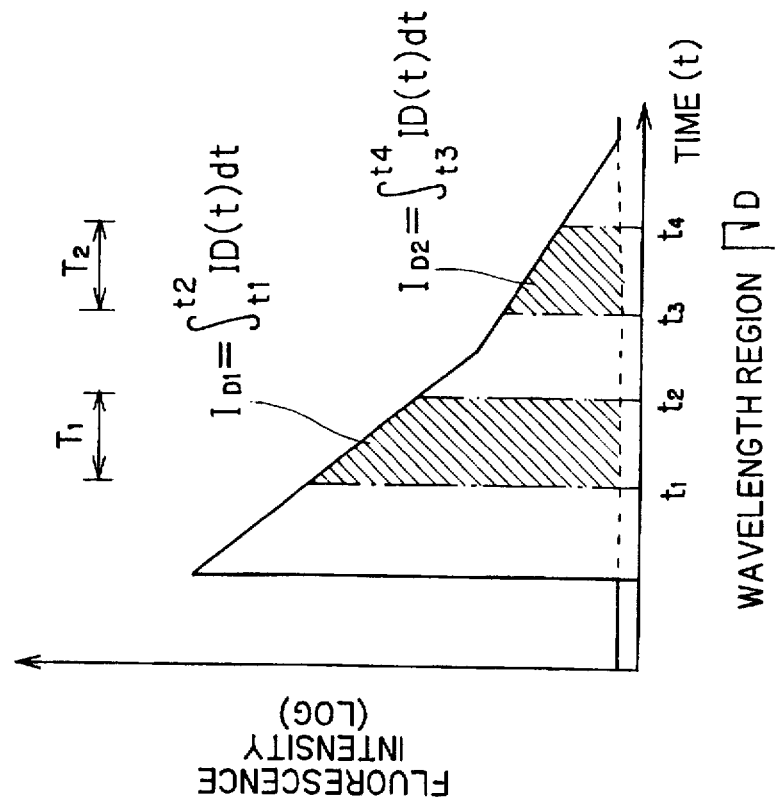
FIG. 9(b) shows temporal change in intensity of fluorescence of wavelength region $\Gamma_A$ of the fluorescence of FIG. 8.

FIG. 8 shows temporal changes in intensity of fluorescence totally generated from the sample including both the donor and acceptor. The fluorescence intensity is determined for the first time period $T_1$ and the second time period $T_2$ as indicated by the shaded portion of the graph in FIG. 8. In the device of the present invention, the fluorescence is divided into light of different wavelengths when it passes through the transmission filters 201 and 202. As shown in FIG. 9, the fluorescence of the donor wavelength region (FIG. 9(a)) and of the acceptor wavelength region (FIG. 9(b)) is inputted to the image intensifiers 101a and 101b respectively where it is multiplied. By integrating the fluorescence over the first time period $T_1$ and the second time period $T_2$, the fluorescence intensities $I_{D1}$, $I_{D2}$, $I_{A1}$, and $I_{A2}$ indicated by the shaded portions of FIG. 9(a) and 9(b) can be measured and calculated.

When the sample includes not only free donors and free acceptors but also donors and acceptors under energy transfer conditions, the temporal changes in fluorescent intensities shown in FIGS. 8 and 9 vary, and the fluorescence intensities $I_{D1}$, $I_{D2}$, $I_{A1}$, and $I_{A2}$ over the time periods $T_1$ and $T_2$ also vary. Thus, detection of these intensities $I_{D1}$, $I_{D2}$, $I_{A1}$, and $I_{A2}$ can provide information on energy transfer occurring in the sample.

The manner of obtaining information on energy transfer will be described according to the present invention.

The information relating to the presence or absence of energy transfer and/or the amount of energy transfer is obtained from the fluorescence intensities $I_{D1}$, $I_{D2}$, $I_{A1}$, and $I_{A2}$ through the calculation described below.

First, a parameter Z of the fluorescence intensity is calculated using the following formula 1:

$$Z=\{(I_{D2}/I_{D1})-(I_{A2}/I_{A1})\}/(I_{D2}/I_{D1}) \qquad \text{(Formula 1)}$$

One method of performing this calculation is with a calculation device 50c having the circuitry shown in FIG. 10. The parameter Z is calculated by first inputting the fluorescence intensities $I_{D1}$, $I_{D2}$, $I_{A1}$, and $I_{A2}$ into this structure including three division circuits 501C, 502C and 504C and a subtraction circuit 503C. The parameter Z outputted from this circuitry is then inputted to the determination circuit 505c where it is judged whether parameter Z is greater than a threshold value $Z_0$. If so, then energy transfer is determined to have taken place in the sample. If parameter Z is determined to be lower than the threshold value $Z_0$ then energy transfer is determined not to have taken place.

The threshold value $Z_0$ is determined based on various information previously known about energy transfer in the sample, such as the first time period $T_1$; the second time period $T_2$; the wavelengths $\lambda_1$, $\lambda_2$, and $\lambda_3$; the fluorescence lifetimes $\tau_{F-D}$ and $\tau_{F-A}$ of the donor and acceptor under free conditions; the ratio $N_D/N_A$ between the number of donor molecules and the number of acceptor molecules in the sample; the ratio F/B between the number of donor molecules under free conditions and the number of donor molecules under energy transfer condition; and energy transfer efficiency E* defined by an equation of $E^*=1-(\tau_{E-DA}/\tau_{F-D})$ where $\tau_{E-DA}$ is the fluorescence lifetime of the donor under energy transfer condition. It is noted that the energy transfer efficiency E* depends on the sixth power $r^6$ of the distance r between the donor and the acceptor.

The relationship between the above-listed values $T_1$, $T_2$, $\lambda_1$, $\lambda_2$, $\lambda_3$, $\tau_{F-D}$, $\tau_{F-A}$, $N_D/N_A$, F/B, and E*; and the fluorescent intensities $I_{D1}$, $I_{D2}$, $I_{A1}$, and $I_{A2}$ (i.e., the parameter Z) will be described below.

FIG. 11(a) shows temporal changes in fluorescence intensity $I_a$(t) of donor wavelength region $\Gamma_D$ emitted from free donor when the excitation light is irradiated at time $t_0$. FIG. 11(b) shows temporal changes in fluorescence intensity $I_b$(t) of donor wavelength region $\Gamma_D$ emitted from free acceptor when the excitation light is irradiated at time $t_0$. FIG. 11(c) shows temporal changes in fluorescence intensity $I_c$(t) of acceptor wavelength region $\Gamma_A$ emitted from free donor when the excitation light is irradiated at time $t_0$. FIG. 11(d) shows temporal changes in fluorescence intensity $I_d$(t) of acceptor wavelength region $\Gamma_A$ emitted from free acceptor when the excitation light is irradiated at time $t_0$.

As apparent from the figures, fluorescence from both the free donor and the free acceptor attenuates with passage of time until the fluorescence from the free acceptor attains an intensity of zero at time point $t_{F-A-end}$ and the fluorescence from the free donor attains an intensity of zero at time point $t_{F-D-end}$. The temporal attenuation in each of these intensities can be expressed using the following Formulas 2 through 5:

| | |
|---|---|
| $I_a(t)=A\ exp\ (-t/\tau_{F-D})$ | (Formula 2) |
| $I_b(t)=0$ | (Formula 3) |
| $I_c(t)=C\ exp\ (-t/\tau_{F-D})$ | (Formula 4) |
| $I_d(t)=D\ exp\ (-t/\tau_{F-A})$ | (Formula 5) | wherein A, C, and D are constants.

It is noted that if $\tau_{F-D}$, $t_{F-D-end}$, $\tau_{F-A}$, or $t_{F-A-end}$ is unknown, they can be obtained by the measurement device of the present invention. The sample including the free donor is set in the device and attenuation in intensity of fluorescence from free donor is detected. Similarly, the sample including the free acceptor is set in the device, and attenuation in intensity of fluorescence from the free acceptor is detected. Based on these detected results, the fluorescence lifetimes $\tau_{F-D}$ and $\tau_{F-A}$ and the fluorescence attenuation completion time points $t_{F-D-end}$ and $t_{F-A-end}$ under free conditions are calculated.

Energy transfer will occur when the donor and acceptor are excited when present in the sample in close proximity within about 8 nm from each other. When energy transfer occurs, temporal changes in fluorescence from donor and acceptor vary.

FIG. 11(e) shows temporal changes in fluorescence intensity $I_e$(t) of donor wavelength region $\Gamma_D$ emitted from energy transferring donor. FIG. 11(f) shows temporal changes in fluorescence intensity $I_f(t)$ of donor wavelength region $\Gamma_D$ emitted from energy transferring acceptor. FIG. 11(g) shows temporal changes in fluorescence intensity $I_g(t)$ of acceptor wavelength region $\Gamma_A$ emitted from energy transferring donor. FIG. 11(h) shows temporal changes in fluorescence intensity $I_h(t)$ of acceptor wavelength region $\Gamma_A$ emitted from energy transferring acceptor.

Thus, fluorescence from both the donor and the acceptor, between which energy transfer occurs, attenuates with passage of time until the fluorescence from both the donor and acceptor attains an intensity of zero at time point $t_{E-DA-end}$. It is apparent from these figures that when energy transfer occurs from the donor to the acceptor, an amount of time required for the donor fluorescence intensity to attain an intensity of zero decreases, and an amount of time required for the acceptor fluorescence intensity to attain an intensity of zero increases.

The attenuation in each of these intensities over time t can be expressed using the following Formulas 6 through 9:

$$I_e(t) = E \exp(-t/\tau_{E-DA}) \quad \text{(Formula 6)}$$

$$I_f(t) = 0 \quad \text{(Formula 7)}$$

$$I_g(t) = G \exp(-t/\tau_{E-DA}) \quad \text{(Formula 8)}$$

$$I_h(t) = H_1 I_d(t) + H_2 I_e(t) \quad \text{(Formula 9)}$$

wherein E, G, $H_1$, and $H_2$ are constants, and $\tau_{E-DA}$ is the fluorescence lifetime of the energy transferring donor.

It is apparent that energy transfer shortens the donor fluorescence lifetime. In other words, the donor fluorescence lifetime $\tau_{E-DA}$ under energy transfer condition is shorter than the lifetime $\tau_{F-D}$ under free condition.

It is noted that if $\tau_{E-DA}$ or $\tau_{E-DA-end}$ is unknown, they can also be obtained by the measurement device of the present invention. The sample including the donor and the acceptor under the energy transfer condition is set in the device and attenuation in intensity of fluorescence from donor and acceptor is detected. Based on the detected results, the fluorescence lifetime $\tau_{E-DA}$ and the fluorescence attenuation completion time points $t_{E-DA-end}$ under energy transfer condition is calculated.

Generally, the sample to be measured contains free donor, free acceptor and donor and acceptor in which energy transfer occurs. In this case, fluorescence from donor and acceptor caused by energy transfer shown in FIGS. 11(e) –11(h) is observed in addition to the fluorescence of the free donor and free acceptor shown in FIGS. 11(a)–11(d).

In order to measure the energy transfer thus occurring in the sample, therefore, as shown in FIGS. 11(a) through (h), the first time period $T_1$ is set to begin after time point $t_{F-A-end}$ and to end before time point $t_{E-DA-end}$ (i.e., $t_{F-A-end} < T_1 < t_{E-DA-end}$), and the second time period $T_2$ is set to begin after time point $t_{E-DA-end}$ and to end before the time point $t_{F-D-end}$ (i.e., $t_{E-DA-end} < T_2 < t_{F-D-end}$). In other words, the timings t1 and t2 defining the time period $T_1$ therebetween and the timings t3 and t4 defining the time period $T_2$ therebetween satisfy the following inequalities: $t_{F-A-end} < t1$, $t2 < t_{E-DA-end}$, $t_{E-DA-end} < t3$, and $t4 < t_{F-D-end}$. These time period settings cause fluorescence emitted from the energy-transferring donor not to be observed over the second time period $T_2$ at wavelength region $\Gamma_D$ or at wavelength region $\Gamma_A$ (FIGS. 11(e) and (g)). These time period settings also cause the fluorescence emitted from the energy-accepting acceptor over the first time period $T_1$ at wavelength region $\Gamma_A$ to be observed (FIG. 11(h)).

It is noted that because the fluorescence lifetimes $\tau_{F-D}$, $\tau_{F-A}$, and $\tau_{E-DA}$ and the attenuation completion time points $t_{F-A-end}$, $t_{E-DA-end}$, and $t_{F-D-end}$ are known or measured by the measuring device of the present invention, the time periods $T_1$ and $T_2$ can be easily determined. For example, when using the above-described IEADANS and TRITC for the donor and the acceptor, it can be determined that $T_1$ is set between 9 and 12 ns and $T_2$ is set between 21 and 27 ns. In other words, t1=9 ns, t2=12 ns, t3=21 ns, and t4=27 ns, where t0 (excitation irradiation timing)=0 ns.

Based on these time period settings, the values $I_{D1}$, $I_{D2}$, $I_{A1}$, and $I_{A2}$ have the following relationships with the values $T_1$, $T_2$, $\lambda_1$, $\lambda_2$, $\lambda_3$, $\tau_{F-D}$, $\tau_{F-A}$, $N_D/N_A$, F/B, and E*.

$$E^* = 1 - (\tau_{E-DA}/\tau_{F-D}) \quad \text{(Formula 10)}$$

$$\int^\infty (I_a(t)) dt \times 5\% = \int^\infty (I_c(t)) dt \quad \text{(Formula 11)}$$

$$F/B = \int^\infty (I_a(t)) dt / \int^\infty (I_e(t)) dt \quad \text{(Formula 12)}$$

$$F/B = \int^\infty (I_c(t)) dt / \int^\infty (I_g(t)) dt \quad \text{(Formula 13)}$$

$$F/B = \int^\infty (I_d(t)) dt / \int^\infty (I_h(t)) dt \quad \text{(Formula 14)}$$

$$N_D/N_A = 1 \text{ (for example) } \quad \text{(Formula 15)}$$

$$I_{D1} = \int^{T_1} (I_a(t)) dt + \int^{T_1} (I_e(t)) dt \quad \text{(Formula 16)}$$

$$I_{D2} = \int^{T_2} (I_a(t)) dt + \int^{T_2} (I_e(t)) dt \quad \text{(Formula 17)}$$

$$I_{A1} = \int^{T_1}(I_c(t)) dt + \int^{T_1} (I_g(t)) dt + \int^{T_1} (I_d(t)) dt + \int^{T_1} (I_h(t)) dt \quad \text{(Formula 18)}$$

$$I_{A2} = \int^{T_2}(I_c(t)) dt + \int^{T_2}(I_d(t)) dt + \int^{T_2}(I_g(t)) dt + \int^{T_2}(I_h(t)) dt \quad \text{(Formula 19)}$$

wherein each of the values $\int^{T_2}(I_e(t)) dt$, $\int^{T_1}(I_d(t)) dt$, $\int^{T_2}(I_d(t)) dt$, $\int^{T_2}(I_g(t)) dt$, and $\int^{T_2}(I_h(t)) dt$ is almost equal to zero.

Because the parameter Z is defined by the values $I_{D1}$, $I_{D2}$, $I_{A1}$, and $I_{A2}$ according to the Formula 1, the parameter Z have the relationships with the values $T_1$, $T_2$, $\lambda_1$, $\lambda_2$, $\lambda_3$, $\tau_{F-D}$, $\tau_{F-A}$, $N_D/N_A$, F/B, and E*, that are determined by the formulas 1 and 10–19.

Figure 12:
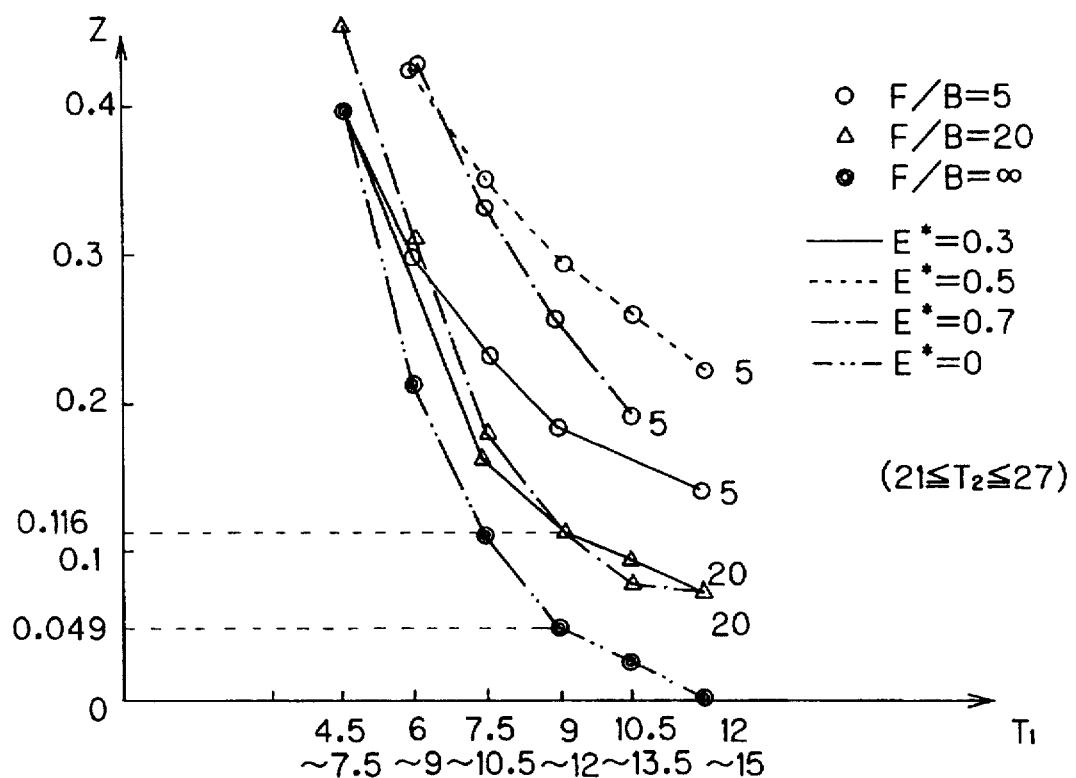
FIG. 12 shows relationship between the parameter Z and the time period T1, the F/B and the E*.
Figure 13:
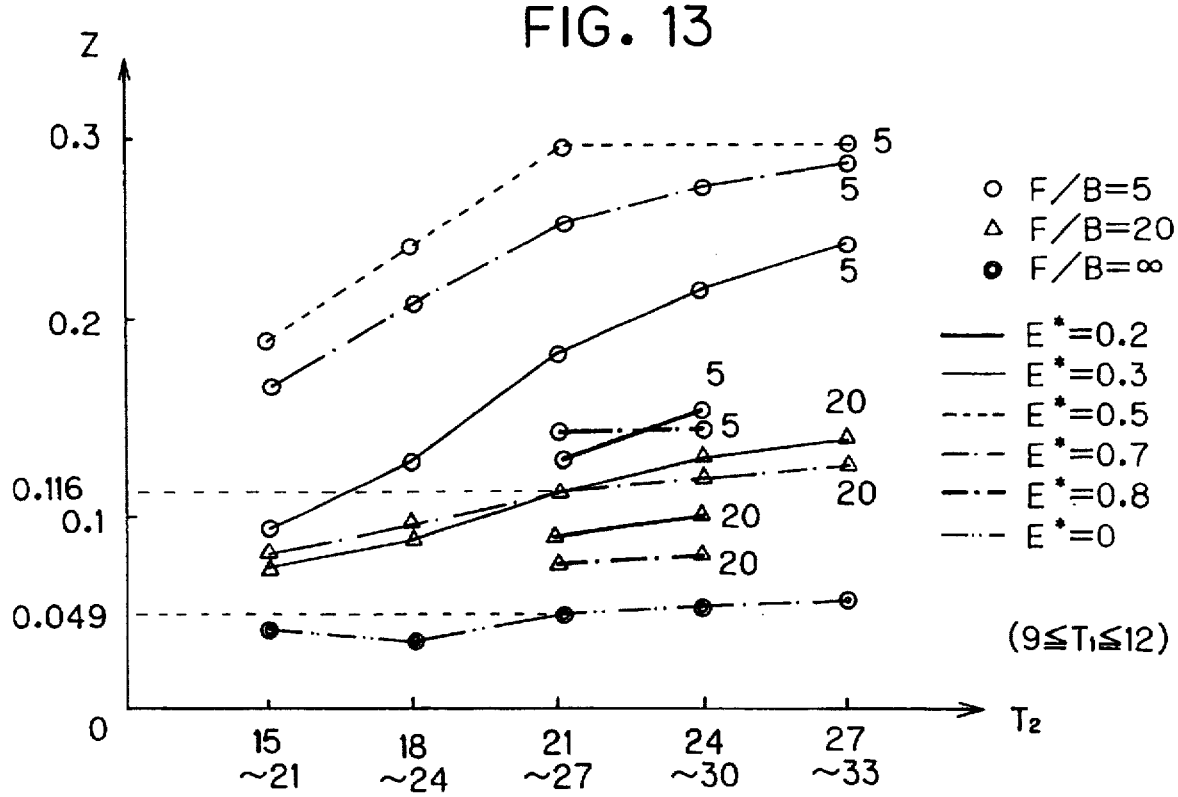
FIG. 13 shows relationship between the parameter Z and the time period T2, the F/B and the E*.

FIGS. 12 and 13 show the relationships between the parameter Z and the values $T_1$ and $T_2$, F/B, and E*, where the other values $\lambda_1$, $\lambda_2$, $\lambda_3$, $\tau_{F-D}$, $\tau_{F-A}$, and $N_D/N_A$ are fixed to 460 nm, 510 nm, 530 nm, 15.0 ns, 1.5 ns, and 1, respectively. It is noted that these values are for measuring the IEADANS and the TRITC. FIG. 12 shows how parameter Z changes dependently on the first time period $T_1$ when the second time period $T_2$ is set to extend between 21 and 27 ns after the pulse of excitation light. FIG. 13 shows how parameter Z changes dependently on the second time period $T_2$ when the first time period $T_1$ is set to extend between 9 and 12 ns after the pulse of excitation light. Each of the figures shows several lines for the case where the values F/B and E* have several values.

It can be understood from the figures that when energy transfer occurs between the donor and acceptor, parameter Z equals or exceeds 0.049. Accordingly, by setting the threshold value $Z_0$ to 0.049 for the measurement of IEADANS and TRITC, the energy transfer measuring device 1 shown in FIG. 2 or FIG. 3 will determine that energy transfer is present when the measured and calculated parameter Z equals or exceeds the threshold value $Z_0$ or absent when the measured and calculated parameter Z is less than the threshold value $Z_0$.

It can also be determined from FIGS. 12 and 13 that when energy transfer is occurring in molecules (IEADANS and TRITC) at an energy transfer efficiency E* of 0.3 to 0.7, the value of parameter Z becomes larger than 0.116. Accordingly, by setting another threshold value $Z_1$ of 0.116 when measuring IEADANS and TRITC, the energy transfer measuring device 1 shown in FIG. 2 or FIG. 3 will determine that energy transfer is occurring at an energy transfer efficiency E* of 0.3 to 0.7 when the measured and calculated parameter Z exceeds the threshold value $Z_1$ or not occurring when the measured and calculated parameter Z is less than the threshold value $Z_1$.

Figure 14:
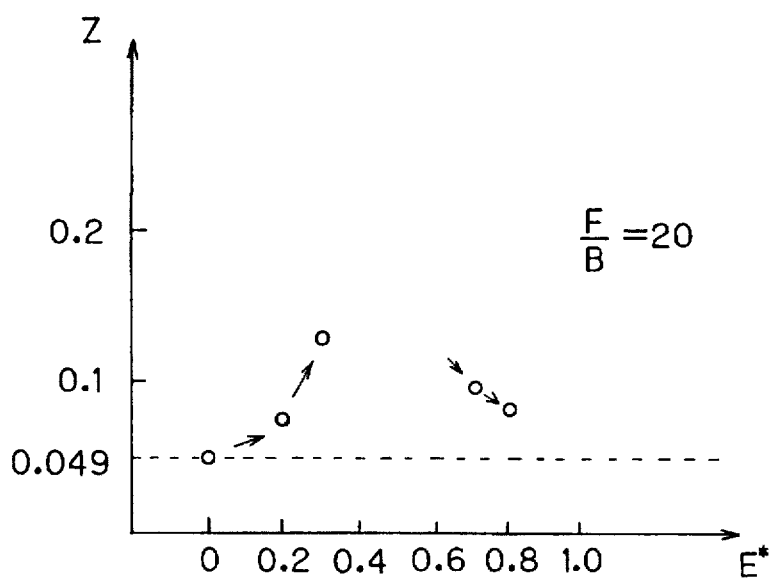
FIG. 14 shows relationship between the parameter Z and the E*.

FIG. 14 shows that parameter Z is directly dependent on the energy transfer efficiency E* when both F/B is fixed to 20 and the second time period $T_2$ is set between 21 and 27 ($21 \leq T_2 \leq 27$). The graph further shows that when the measured parameter Z is equal to or less than the threshold value $Z_0$ of 0.049, then energy transfer is determined not to be present. FIG. 14 further shows that when measured parameter Z is equal to or greater than a threshold value $Z_1$ of 0.116, the energy transfer efficiency E* of the occurring energy transfer is 0.3 or 0.7 or therebetween (i.e., $0.3 \leq E^* \leq 0.7$). Because the energy transfer efficiency E* is inversely proportional to the sixth power of the distance r between the donor and the acceptor (i.e., $r^6$), the range of the distance r can also be determined based on the thus determined range of the energy transfer efficiency E*. Similarly, if any other values (such as F/B or $N_D/N_A$) are unknown, the ranges of these values can be calculated. Thus, any information related to energy transfer can be obtained.

Experiments were performed using the device shown in FIG. 3 to determine information on energy transfer between IEADANS (referred to as fluorescent molecule D hereinafter) and TRITC (referred to as fluorescent molecule A hereinafter).

Figure 15:
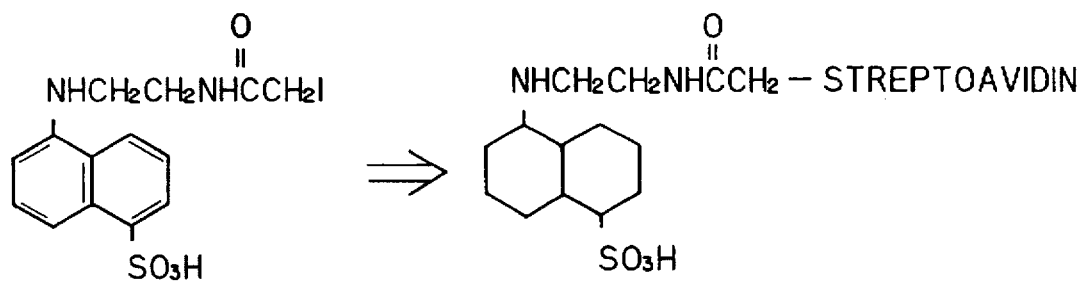
FIG. 15 shows how IEADANS is tagged with streptoavidin in a first sample.
Figure 16:
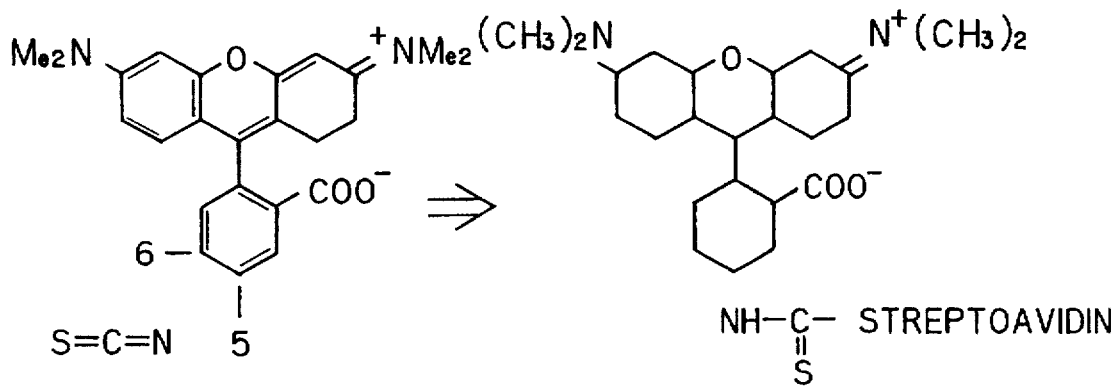
FIG. 16 shows how TRITC is tagged with streptoavidin in a first sample.

First, a first sample of streptoavidin (protein) tagged with fluorescent molecule D as shown in FIG. 15 was prepared. Then, a second sample of streptoavidin tagged with fluorescent molecule A as shown in FIG. 16. A third sample of streptoavidin tagged with both fluorescent molecule D and fluorescent molecule A was prepared. In the third sample, molecules A and D were tagged to positions of the streptoavidin close enough for energy transfer to occur.

Then, the fluorescence lifetime $\tau_{F-D}$ and $\tau_{F-A}$ of fluorescent molecules A and D under free condition was measured with the energy transfer instrument 1 shown in FIG. 3. That is, a sample solution containing the first sample was set on the sample setting glass 30a. Fluorescent intensity was measured while varying the time period at which the image intensifiers 101a and 101b were triggered. Thus, the attenuation in the fluorescent intensity was detected to determine the fluorescence lifetime $\tau_{F-D}$. The same operation was conducted on the second sample to determine its fluorescence lifetime $\tau_{F-A}$. The fluorescence lifetime of the fluorescent molecule D was measured to be 15.0 ns and the fluorescence lifetime of the fluorescent molecule A was measured to be 1.5 ns.

It is noted that based on these measurements, values of the fluorescence attenuation completion timings $t_{F-D-end}$ and $t_{F-A-end}$ for the molecules D and A under free conditions were also obtained. In addition, a sample solution containing the third sample with a relatively high density was set on the sample setting glass 30a. Fluorescent intensity was measured while varying the time period at which the image intensifiers 101a and 101b were triggered. Thus, the attenuation in the fluorescent intensity was detected to determine the fluorescence lifetime $\tau_{E-DA}$ and the attenuation completion time point $t_{E-DA-end}$. Based on these obtained time point values $t_{F-D-end}$, $t_{E-DA-end}$ and $t_{F-A-end}$, the first and second time periods $T_1$, $T_2$ were determined so that these values have the following relationships:

$$0 < t_{F-A-end} < T_1 < t_{F-D-end} < T_2 < t_{F-D-end}$$

where 0 indicates the timing at which the excitation light is irradiated on the sample.

According to this experiments, the first time period $T_1$ was set between 9 and 12 ns from the excitation light irradiation timing, and the second time period $T_2$ was set between 21 and 27 ns from the excitation light irradiation timing.

Then, in order to measure the energy transfer, the device of FIG. 3 was set up as follows. A nitrogen laser 40a was provided for exciting samples with a 337 nm wavelength laser beam. A filter 201 was provided for allowing passage of a wavelength region $\Gamma_1$ spanning 460 to 510 nm. A filter 202 was provided for allowing passage of a wavelength region $\Gamma_2$ from 530 nm and longer. The first time period $T_1$ for operation of the image intensifier 101a was set between 9 and 12 ns. The second time period $T_2$ for operation of the image intensifier 101b was set between 21 and 27 ns.

In a first experiment, the fluorescence intensities $I_{D1}$, $I_{D2}$, $I_{A1}$, and $I_{A2}$ were measured for a sample solution containing 1 μM of the first sample and 1 μM of the second sample. In this sample solution, energy transfer did not occur from the fluorescent molecule D to the fluorescent molecule A. The following fluorescence intensities were measured in the first experiment:

$$I_{D2}/I_{D1} = 0.820$$

$$I_{A2}/I_{A1} = 0.780.$$

In a second experiment, the fluorescence intensities $I_{D1}$, $I_{D2}$, $I_{A1}$, and $I_{A2}$ were measured for a sample solution containing 1 μM of the first sample, 1 μM of the second sample, and 0.05 μM of the third sample. Of all molecules in the sample, energy transfer occurred in 5% of the sample solution and did not occur in 95%. Accordingly, the ratio F/B was 20. The following fluorescence intensities were measured in the second experiment:

$$I_{D2}/I_{D1} = 0.741$$

$$I_{A2}/I_{A1} = 0.601.$$

The values for parameter Z calculated by the calculation device 50c from the first and second experiments were:

Z=0.049 (First Experiment)

Z=0.189. (Second Experiment)

By comparing the calculated values Z with the threshold value $Z_0$ of 0.049, it could be determined that energy transfer did not occur in any molecules during the first experiment and that energy transfer did occur in some molecules during the second experiment. By comparing the calculated values Z with the threshold value $Z_1$ of 0.116, it could be further determined that energy transfer of an energy transfer efficiency E* of between 0.3 and 0.7 occurred in the second experiment. Because the energy transfer efficiency E* is inversely proportional to the sixth power of the distance r between positions on the streptoavidin where the donor and the acceptor were tagged can be determined.

Figure 17:
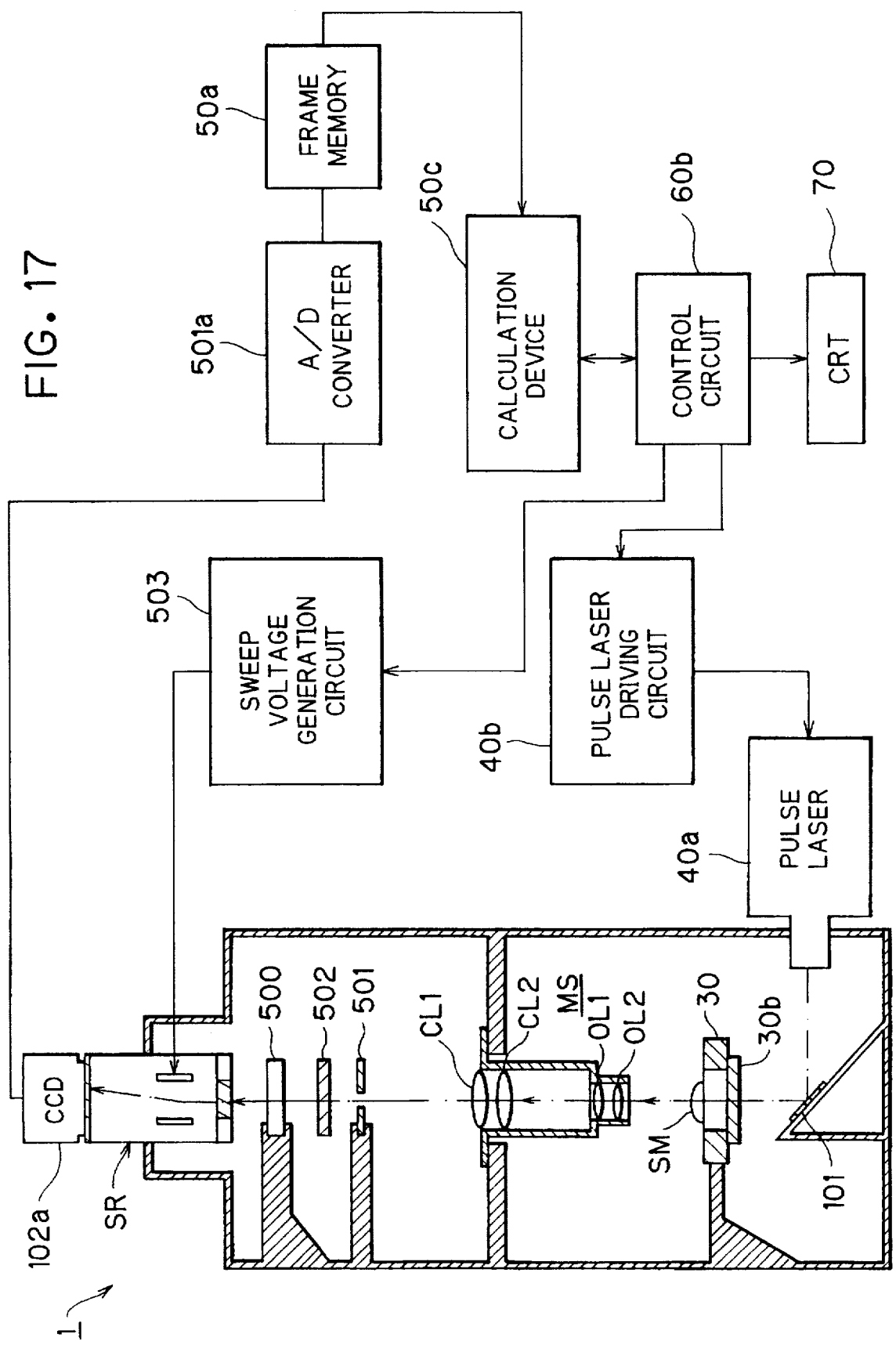
FIG. 17 shows a structure of another detailed example of the energy transfer measuring device of the embodiment.

Next, an energy transfer device 1 according to a second example of the present embodiment will be described while referring to FIGS. 17 and 18. In the first example, as shown in FIG. 3, the device is provided with two wavelength selective filters for dividing the fluorescence by wavelength and with two image intensifiers for picking up the fluorescence of each wavelength over each time period. Contrarily, in the second example, a single diffraction grating or prism is used to divide the fluorescence by wavelength, and a single streak tube is used for picking up the fluorescence of each wavelength over each time period.

An energy transfer measuring device with this structure will be described while referring to FIG. 17. The gas laser 40a (nitrogen laser, for example) is pulsingly driven by the pulse laser drive circuit 40b. The sample SM generates fluorescence when irradiated. The fluorescence is collected by the microscope MS so as to be incident on a streak tube SR after passing through a slit 501, an excitation cut filter 502, and a diffraction grating (prism) 500. The excitation light cut filter 502 is for cutting off the excitation light (coherent light from the nitrogen gas laser). The excitation light will become noise for the weak fluorescence that has passed through the filter. The diffraction grating spatially divides the fluorescence that has passed through the filter into the wavelength regions $\Gamma_D$ and $\Gamma_A$.

Accordingly, fluorescence, spatially spreading according to its wavelength, is incident on the streak tube SR. Streak tubes from the N3373 streak tube series produced by Hamamatsu Photonics are suitable for use as the streak tube SR. The time period for measurement can be set at picosecond to femtosecond time intervals. The streak tube SR includes a photoelectric surface on which the fluorescence is incident. Electrons resulting from photoelectric conversion of the fluorescence are deflected by deflection electrodes. A fluorescing surface for converting the electrons back to fluorescence is provided at the output of the streak tube SR. The time period is set by the sweep voltage applied to the deflecting electrodes for scanning the electrons. The sweep voltage is supplied to the deflecting electrodes from a sweep voltage generation circuit 503. The fluorescence outputted from the streak tube SR is picked up as an image by the same CCD camera 102a shown in FIG. 3.

Figure 18:
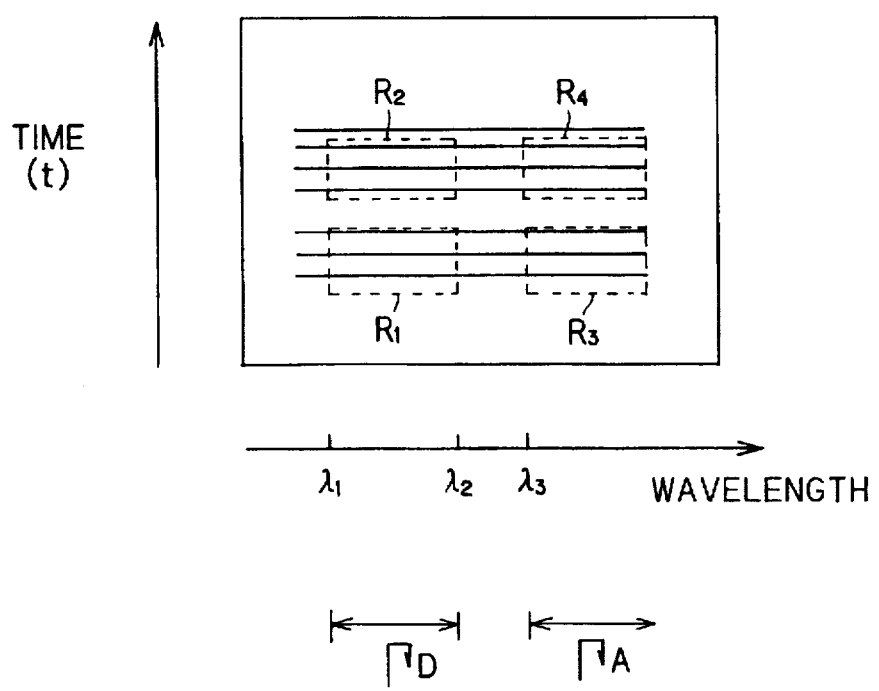
FIG. 18 illustrates how fluorescent images for the two wavelength regions at the two time periods are separated to be incident on an image receiving region of the CCD camera of the device of FIG. 17.

FIG. 18 shows representation of a fluorescence image incident on the light receiving region of the CCD camera 102a. The fluorescence image is divided horizontally into separate wavelengths by the diffraction grating 500 and vertically into time periods by the sweep of the streak tube SR. The fluorescence intensity of the regions corresponding to reception regions R1 through R4 are respectively accumulated in the calculation circuit 50c to determine the fluorescence intensities $I_{D1}$, $I_{D2}$, $I_{A1}$, and $I_{A2}$. Other components of the energy transfer device shown in FIG. 17 are the same as those shown in FIG. 3. Information relating to energy transfer can be obtained from the fluorescence intensities $I_{D1}$, $I_{D2}$, $I_{A1}$, and $I_{A2}$. The fluorescence intensities and energy transfer information are sent to the controller 60b and displayed on the CRT 70.

With the device according to the second example, time periods can be set with a high degree of precision using the streak tube SR. Also, because a diffraction grating 500 is used for dividing the fluorescence by wavelength, the fluorescence from the donor can be divided from the fluorescence from the acceptor using the same CCD camera 102a. This insures that fluorescence from the donor and from the acceptor are measured simultaneously with no difference in the time periods that may be caused when these are measured by separate units.

While the invention has been described in detail with reference to specific embodiments thereof, it would be apparent to those skilled in the art that various changes and modifications may be made therein without departing from the spirit of the invention, the scope of which is defined by the attached claims.

For example, in the above described embodiment, whether energy transfer occurred is determined using the parameter Z. However, it would be convenient to define other parameter functions determined based on various test results for each fluorophore sample. An experimenter could then simply refer to values of the parameter functions (for example, $Z \leq Z_0$) to easily determine his/her required information.

Although IEADANS and TRITC are suggested as a donor/acceptor combination, any combination can be used as long as the donor has a fluorescence lifetime $\tau_{F-D}$ longer than that $\tau_{F-A}$ of the acceptor, and the fluorescence spectrum of the donor overlaps the absorption spectrum of the acceptor. For example, fluorescein and tetramethylrhodamin make a good combination with a fluorescence lifetime ratio of four.

With this method, it is possible to detect the energy transfer occurring in only a small amount of the molecules in the entire sample, even though energy transfer does not occur in most of the molecules of the sample.

The above-described measurement of energy transfer of the present invention is a very effective when applied to in vivo detection of substances present in only small quantities. The energy transfer method is applicable to a method in which probes (i.e., donor and acceptor molecules that bind with the objective substance in a particular way) are added to the objective substance. Examples of probes are antibodies for when the objective molecule is a protein or complementary oligonucleotides for when the objective molecule is DNA or RNA. By detecting the energy transfer between the probes, the amount of the objective substance that combined with the probes are measured. Sometimes, large amount of free probes (free donors and free acceptors) that are not in combination with the objective molecule or substance are present in the living cell under investigation. Although the free probes can be washed out when the measurement is made in vitro, this is not possible with in vivo measurements. In vivo measurement has to be conducted under conditions where many free donor molecules are present.

When only a small amount of the objective molecules or substances to be bound with probes are present, sometimes the probes will be absorbed in a manner other than the particular way described above. The signal from probes that are bound with objective molecules in the characteristic manner differs from the signal from free probes or from probes absorbed by the objective molecule in an uncharacteristic manner. By applying this phenomenon to the energy transfer method of the present invention, experiments can be designed so that the signal generated from probe characteristically bound with subject molecule will change when probe binds characteristically with subject molecule. For example, when the base sequence in an DNA or RNA is under investigation, two types of oligonucleotide probe, tagged with different fluorescent reagents at their terminals, are prepared. By attaching these probes to different regions about two to seven bases apart on the objective DNA or RNA through hybridization, the objective DNA or RNA can be detected by measuring the energy transfer between the two fluorescent probes. This detection method is described by Heller, M. J et al., in European Patent Application Publication No.070685 in 1983 and by Heller, M. J and Jablonski E. J. in European Patent Application Publication No. 229943 in 1987.

Under conditions such as in vivo when the unbound probe can not be washed away, many molecules in which energy transfer does not occur will be present in the sample. Because of this, energy transfer has been conventionally unapplicable to this type of DNA sequencing. The energy transfer device and method according to the present invention solve this problem so that measurement of energy transfer is possible even under conditions such as in vivo when unbound probe can not be washed away.

According to the present invention, the energy transfer device and method of the present invention, fluorescence generated by excitation light is measured after being divided using, for example, a wavelength divider into at least two different wavelength regions. Additionally, the fluorescence of each different wavelength region is measured over at least two different time periods. Therefore, even when molecules in which energy transfer does not occur are present in great amounts, the existence of only a small number of molecules in which energy transfer occurs can be detected. Also, according to the device for measuring energy transfer of the present invention, identification of a parameter that determines whether energy transfer is present or the amounts and nature of various substances in small quantities can be performed. Because energy transfer is particularly dependent on the distance between the fluorophores, nucleic acid base sequences can be determined with greater precision by measuring information on energy transfer of fluorophores tagged with hybridized complementary nucleic acids during analysis of genetic information such as the present or existence of genetic expression or change in the primary structure of DNA or RNA.

What is claimed is:

1. A method of measuring energy transfer between donor fluorophores and acceptor fluorophores under energy-transfer condition included in a sample, the sample also including donor fluorophores and acceptor fluorophores under non-energy-transfer condition, the method comprising the steps of:

irradiating, with excitation light, a sample including donor fluorophores and acceptor fluorophores both under non-energy-transfer condition and under energy-transfer condition, so that the donor fluorophores and the acceptor fluorophores emit fluorescence, the donor fluorophores and the acceptor fluorophores emitting fluorescence of different wavelength bands which are partly overlapped with each other, the donor fluorophores having fluorescence lifetime longer than a fluorescence lifetime of the acceptor fluorophores, wherein intensity of fluorescence from the acceptor fluorophores attenuates over time after the irradiation of the excitation light, in accordance with its fluorescent lifetime, the attenuation occurring so that the intensity of fluorescence from the acceptor fluorophores is below a predetermined threshold at a first timing, intensity of fluorescence from the donor fluorophores attenuates over time after the irradiation of the excitation light, in accordance with its fluorescent lifetime, the attenuation occurring so that the intensity of fluorescence from the donor fluorophores is below a second predetermined threshold at a second timing, the fluorescence lifetime of the donor fluorophores varies when energy transfer occurs from the donor fluorophores to the acceptor fluorophores so that the intensity of fluorescence from the donor fluorophores attenuates over time when the energy transfer occurs after the irradiation of the excitation light, in accordance with its varied fluorescent lifetime, the attenuation occurring so that the intensity of fluorescence from the donor fluorophores is below a third predetermined threshold at a third timing different from the second timing;

dividing light, emitted from the sample, into a first light of a first wavelength and a second light of a second wavelength, the first wavelength region being only within the fluorescence wavelength band of the donor fluorophores, the second wavelength region being set not only within the fluorescence wavelength band of the acceptor fluorophores but also within a predetermined amount of a part of the fluorescence wavelength band of the donor fluorophores;

measuring an intensity of the first light and an intensity of the second light over a first time period, which is determined between the first timing and the third timing, to thereby obtain a total intensity $I_{D1}$ of the first light over the first time period and a total intensity $I_{A1}$ of the second light over the first time period;

measuring an intensity of the first light and an intensity of the second light over a second time period, which is determined between the third timing and the second timing, to thereby obtain a total intensity $I_{D2}$ of the first light over the second time period and a total intensity $I_{A2}$ of the second light over the second time period; and determining energy transfer, occurring between the donor fluorophores and the acceptor fluorophores based on a ratio between the amounts $I_{D2}$ and $I_{D1}$ and a ratio between the amounts $I_{A2}$ and $I_{A1}$.

2. The method as claimed in claim 1, wherein the total intensity amounts $I_{D1}$ and $I_{A1}$ are obtained through opening gates of first and second light detectors during the first time period, the first and second light detectors being located to be capable of respectively receiving the first light and the second light, the gate-opened first and second light detectors detecting the intensities of the first light and the second light over the first time period, the intensities of the first and second lights detected during the first time period being integrated over the first time period, and wherein the intensities $I_{D2}$ and $I_{A2}$ are obtained through opening gates of the first and second light detectors during the second time period, the gate-opened first and second light detectors detecting the intensities of the first light and the second light during the second time period, the intensities of the first and second lights detected during the second time period being integrated over the second time period.

3. The method as claimed in claim 2, wherein the first and second lights, with their intensities being detected during the first time period, are converted into first and second electric signals and integrated over the first time period into the amounts $I_{D1}$ and $I_{A1}$, respectively, and wherein the first and second lights, with their intensities being detected during the second time period, are converted into third and fourth electric signals and integrated over the second time period into the amounts $I_{D2}$ and $I_{A2}$, respectively.

4. The method as claimed in claim 1, wherein the total intensity amounts $I_{D1}$ and $I_{A1}$ are obtained through inputting trigger signals to first and second image intensifiers during the first time period, the first and second image intensifiers being located capable of respectively receiving the first light and the second light, the triggered first and second image intensifiers multiplying the intensities of the first light and the second light only during the first time period, the intensities of the first and second lights thus multiplied during the first time period being integrated over the first time period, and wherein the intensities $I_{D2}$ and $I_{A2}$ are obtained through inputting trigger signals to the first and second image intensifiers during the second time period, the triggered first and second image intensifiers multiplying the intensities of the first light and the second light only during the second time period, the intensities of the first and second lights thus multiplied during the second time period being integrated over the second time period.

5. The method as claimed in claim 4, wherein the first and second lights, with their intensities being multiplied during the first time period, are respectively picked up by first and second CCD cameras and converted into first and second electric signals, the first and second electric signals being integrated over the first time period into the amounts $I_{D1}$ and $I_{A1}$, respectively, and wherein the first and second lights, with their intensities being multiplied during the second time period, are respectively picked up by the first and second CCD cameras and converted into third and fourth electric signals, the third and fourth electric signals being integrated over the second time period into the amounts $I_{D2}$ and $I_{A2}$, respectively.

6. The method as claimed in claim 5, wherein the first CCD camera has a plurality of first pixels each for receiving a corresponding part of the first light which is multiplied during the first time period and for converting the received light into a first electric charge, each first pixel again receiving a corresponding part of the first light which is multiplied during the second time period and converting the received light into a third electric charge, a first frame memory accumulating the first electric charge produced from each first pixel and accumulating the third electric charge produced from each first pixel, a calculation device spatially integrating the first electric charges supplied from all the first pixels to obtain the amount $I_{D1}$ and spatially integrating the third electric charges supplied from all the first pixels to obtain the amount $I_{D2}$, and wherein the second CCD camera has a plurality of second pixels each for receiving a corresponding part of the second light which is multiplied during the first time period and for converting the received light into a second electric charge, each second pixel again receiving a corresponding part of the second light which is multiplied during the second time period and converting the received light into a fourth electric charge, a second frame memory accumulating the second electric charge produced from each second pixel and accumulating the fourth electric charge produced from each second pixel, a calculation device spatially integrating the second electric charges supplied from all the second pixels to obtain the amount $I_{A1}$ and spatially integrating the fourth electric charges supplied from all the second pixels to obtain the amount $I_{A2}$.

7. The method as claimed in claim 1, wherein the total intensity amounts $I_{D2}$ and $I_{A1}$ are obtained through inputting a first sweep voltage to a single streak tube during the first time period, the streak tube being located capable of receiving the first light and the second light into different regions in a first direction, the first sweep voltage-driven streak tube introducing the first light and the second light into first and second positions arranged in the first direction, the intensities of the first and second lights thus introduced into the first and second positions being integrated into the amounts $I_{D1}$ and $I_{A1}$, and wherein the total intensity amounts $I_{D2}$ and $I_{A2}$ are obtained through inputting a second sweep voltage to the streak tube during the second time period, the second sweep voltage-driven streak tube introducing the first light and the second light into third and fourth positions arranged in the first direction, the third and fourth positions being shifted from the first and second positions in a second direction substantially perpendicular to the first direction, the intensities of the first and second lights thus introduced into the third and fourth positions being integrated into the amounts $I_{D2}$ and $I_{A2}$.

8. The method an claimed in claim 7, wherein the first and second lights, introduced into the first and second positions during the first time period, are respectively picked up by corresponding portions of a single CCD camera and converted into first and second electric signals, the first and second electric signals being integrated into the amounts $I_{D1}$ and $I_{A1}$, respectively, and wherein the first and second lights, introduced into the third and fourth positions during the second time period, are respectively picked up by corresponding portions of the CCD camera and converted into third and fourth electric signals, the third and fourth electric signals being integrated into the amounts $I_{D2}$ and $I_{A2}$, respectively.

9. The method as claimed in claim 1, wherein a filter divides the light, emitted from the sample, into the first light and the second light.

10. The method as claimed in claim 1, wherein a diffraction grating divides the light, emitted from the sample, into the first light and the second light.

11. The method as claimed in claim 1, wherein the light, emitted from the sample, is divided in a first direction into the first light and the second light, wherein a single streak tube is inputted with a first sweep voltage during the first time period to introduce the received first and second lights into first and second positions arranged in the first direction, wherein the streak camera is inputted with a second sweep voltage during the second time period to introduce the received first and second lights into third and fourth positions arranged in the first direction, the third and fourth positions being shifted from the first and second positions in a second direction almost perpendicular to the first direction, wherein a single CCD camera connected to the streak tube receives the lights introduced to the first, second, third, and fourth positions and produces first, second, third, and fourth electric signals accordingly, and wherein the first, second, third, and fourth electric signals are integrated into the amounts $I_{D1}$, $I_{A1}$, $I_{D2}$, and $I_{A2}$.

12. The method as claimed in claim 1, further comprising the steps of:

measuring attenuation of fluorescence from the acceptor fluorophores under non-energy-transfer condition to determine the first timing;

measuring attenuation of fluorescence from the donor fluorophores under non-energy-transfer condition to determine the second timing; and measuring attenuation of fluorescence from the acceptor fluorophores and the donor fluorophores under energy transfer condition to determine the third timing.

13. The method as claimed in claim 12, wherein the first timing determining step includes the steps of:

irradiating, with excitation light, a first sample including the acceptor fluorophores;

measuring intensity of fluorescence emitted from the first sample; and determining the first timing at which the intensity is attenuated below the first predetermined threshold.

14. The method as claimed in claim 12, wherein the second timing determining step includes the steps of:

irradiating, with excitation light, a second sample including the donor fluorophores;

measuring intensity of fluorescence emitted from the second sample; and determining the second timing at which the intensity is attenuated below the second predetermined threshold.

15. The method as claimed in claim 12, wherein the third timing determining step includes the steps of:

irradiating, with excitation light, a third sample including both the acceptor fluorophores and the donor fluorophores under energy transfer condition;

measuring intensity of fluorescence emitted from the third sample; and determining the third timing at which the intensity is attenuated below the third predetermined threshold.

16. The method as claimed in claim 1, wherein the ratio between the amounts $I_{D2}$ and $I_{D1}$ indicates an attenuation rate of the intensity of the first light, and the ratio between the amounts $I_{A2}$ and $I_{A1}$ indicates an attenuation rate of the intensity of the second light, and wherein the energy transfer, occurring between the donor fluorophores and the acceptor fluorophores under the energy-transfer condition, is represented by a predetermined relationship between the ratio between the amounts $I_{D2}$ and $I_{D1}$ and the ratio between the amounts $I_{A2}$ and $I_{A1}$.

17. The method as claimed in claim 16, wherein the predetermined relationship between the ratio between the amounts $I_{D2}$ and $I_{D1}$ and the ratio between the amounts $I_{A2}$ and $I_{A1}$ is represented by the following formula:

$$\{(I_{D2}/I_{D1})-(I_{A2}/I_{A1})\}/(I_{D2}/I_{D1}).$$

18. A method of measuring energy transfer occurring in a sample which includes donor fluorophores and acceptor fluorophores both under non-energy-transfer condition and under energy-transfer condition, the method comprising the steps of:

measuring a lifetime of fluorescence from acceptor fluorophores under non-energy-transfer condition to determine a first timing, at which intensity of fluorescence from the non-energy-transfer acceptor fluorophores attenuates below a predetermined threshold after irradiation of excitation light;

measuring a lifetime of fluorescence from donor fluorophores under non-energy-transfer condition to determine a second timing, at which intensity of fluorescence from the non-energy-transfer donor fluorophores attenuates below a second predetermined threshold after irradiation of excitation light, the fluorescence lifetime of the donor fluorophores being longer than the fluorescence lifetime of the acceptor fluorophores;

measuring a lifetime of fluorescence from the acceptor fluorophores and the donor fluorophores under energy-transfer condition to determine a third timing, at which intensity of fluorescence from the donor and the acceptor fluorophores attenuates below a third predetermined threshold after irradiation of excitation light;

determining a first time period between the first timing and the third timing and a second time period between the third timing and the second timing;

irradiating, with excitation light, a sample including the donor fluorophores and the acceptor fluorophores under both non-energy-transfer condition and energy-transfer condition, so that the donor fluorophores and the acceptor fluorophores emit fluorescence, dividing light, emitted from the sample, into a first light of a first wavelength and a second light of a second wavelength, the first wavelength region being only within the fluorescence wavelength band of the donor fluorophores, the second wavelength region being not only within the fluorescence wavelength band of the acceptor fluorophores but also within a predetermined amount of a part of the fluorescence wavelength band of the donor fluorophores;

measuring an intensity of the first light and an intensity of the second light over the first time period to thereby obtain a total intensity $I_{D1}$ of the first light over the first time period and a total intensity $I_{A1}$ of the second light over the first time period;

measuring an intensity of the first light and an intensity of the second light over the second time period to thereby obtain a total intensity $I_{D2}$ of the first light over the second time period and a total intensity $I_{A2}$ of the second light over the second time period; and determining energy transfer, occurring between the donor fluorophores and the acceptor fluorophores based on a ratio between the amounts $I_{D2}$ and $I_{D1}$ and a ratio between the amounts $I_{A2}$ and $I_{A1}$.

19. The method as claimed in claim 18, wherein the ratio between the amounts $I_{D2}$ and $I_{D1}$ indicates an attenuation rate of the intensity of the first light, and the ratio between the amounts $I_{A2}$ and $I_{A1}$ indicates an attenuation rate of the intensity of the second light, and wherein the energy transfer, occurring between the donor fluorophores and the acceptor fluorophores under the energy-transfer condition, is represented by a predetermined relationship between the ratio between the amounts $I_{D2}$ and $I_{D1}$ and the ratio between the amounts $I_{A2}$ and $I_{A1}$.

20. The method as claimed in claim 19, wherein the predetermined relationship between the ratio between the amounts $I_{D2}$ and $I_{D1}$ and the ratio between the amounts $I_{A2}$ and $I_{A1}$ is represented by the following formula:

$$\{(I_{D2}/I_{D1})-(I_{A2}/I_{A1})\}/(I_{D2}/I_{D1}).$$

21. A method of measuring energy transfer occurring in a sample which includes donor fluorophores and acceptor fluorophores both under non-energy-transfer condition and under energy-transfer condition, the method comprising the steps of:

measuring a lifetime of fluorescence from acceptor fluorophores under non-energy-transfer condition to determine a first timing, at which intensity of fluorescence from the non-energy-transfer acceptor fluorophores attenuates below a predetermined threshold after irradiation of excitation light;

measuring a lifetime of fluorescence from non-energy-transfer donor fluorophores to determine a second timing, at which intensity of fluorescence from the non-energy-transfer donor fluorophores attenuates below a second predetermined threshold after irradiation of excitation light, the fluorescence lifetime of the donor fluorophores being longer than the fluorescence lifetime of the acceptor fluorophores;

measuring a lifetime of fluorescence from the acceptor fluorophores and the donor fluorophores under energy-transfer condition to determine a third timing, at which intensity of fluorescence from the donor and acceptor fluorophores attenuates below a third predetermined threshold after irradiation of excitation light;

determining a first time period between the first timing and the third timing and a second time period between the third timing and the second timing;

irradiating, with excitation light, a test sample including the donor fluorophores and the acceptor fluorophores only under non-energy-transfer condition so that the donor fluorophores and the acceptor fluorophores emit fluorescence, measuring an intensity of the fluorescence emitted from the test sample in a first wavelength region and a second wavelength region during the first time period, to thereby obtain an intensity $I_{D1}$ of the first wavelength region and intensity $I_{A1}$ of the second wavelength region, the first wavelength region being set only within the fluorescence wavelength band of the donor fluorophores, the second wavelength region being set not only within the fluorescence wavelength band of the acceptor fluorophores but also within a predetermined amount of a part of the fluorescence wavelength band of the donor fluorophores;

measuring an intensity of the fluorescence emitted from the test sample in the first wavelength region and the second wavelength region during the second time period, to thereby obtain an intensity $I_{D2}$ of the first wavelength region and an intensity $I_{A2}$ of the second wavelength region;

determining energy transfer test information Z based on a ratio between the amounts $I_{D2}$ and $I_{D1}$ and a ratio between the amounts $I_{A2}$ and $I_{A1}$;

irradiating, with excitation light, a sample including the donor fluorophores and the acceptor fluorophores under both non-energy-transfer condition and energy-transfer condition, so that the donor fluorophores and the acceptor fluorophores emit fluorescence;

measuring an intensity of the fluorescence emitted from the sample in the first wavelength region and the second wavelength region during the first time period, to thereby obtain an intensity $I_{D1}'$ of the first wavelength region and an intensity $I_{A1}'$ of the second wavelength region;

measuring an intensity of the fluorescence emitted from the sample in the first wavelength region and the second wavelength region during the second time period, to thereby obtain an intensity $I_{D2}'$ of the first wavelength region and an intensity $I_{A2}'$ of the second wavelength region;

determining energy transfer information Z' based on a ratio between the amounts $I_{D2}'$ and $I_{D1}'$ and a ratio between the amounts $I_{A2}'$ and $I_{A1}'$; and determining, based on the energy transfer test information Z and the energy transfer information Z', energy transfer occurring between the donor fluorophores and the acceptor fluorophores under energy-transfer condition in the sample.

22. The method as claimed in claim 21, wherein the ratio between the amounts $I_{D2}$ and $I_{D1}$ indicates an attenuation rate of the intensity of the first light from the test sample, and the ratio between the amounts $I_{A2}$ and $I_{A1}$ indicates an attenuation rate of the intensity of the second light from the test sample, the energy transfer test information Z being represented by a predetermined relationship between the ratio between the amounts $I_{D2}$ and $I_{D1}$ and the ratio between the amounts $I_{A2}$ and $I_{A1}$, and wherein the ratio between the amounts $I_{D2}'$ and $I_{D1}'$ indicates an attenuation rate of the intensity of the first light from the sample, and the ratio between the amounts $I_{A2}'$ and $I_{A1}'$ indicates an attenuation rate of the intensity of the second light from the sample, the energy transfer information Z' being represented by a predetermined relationship between the ratio between the amounts $I_{D2}'$ and $I_{D1}'$ and the ratio between the amounts $I_{A2}'$ and $I_{A1}'$.

23. The method as claimed in claim 22, wherein the predetermined relationship between the ratio between the amounts $I_{D2}$ and $I_{D1}$ and the ratio between the amounts $I_{A2}$ and $I_{A1}$ is represented by the following formula:

$$\{(I_{D2}/I_{D1})-(I_{A2}/I_{A1})\}/(I_{D2}/I_{D1}),$$

and wherein the predetermined relationship between the ratio between the amounts $I_{D2}'$ and $I_{D1}'$ and the ratio between the amounts $I_{A2}'$ and $I_{A1}'$ is represented by the following formula:

$$\{(I_{D2}'/I_{D1}')-(I_{A2}'/I_{A1}')\}/(I_{D2}'/I_{D1}').$$

24. A method of determining whether a certain substance exists in a test sample, the method comprising the steps of:

preparing a donor fluorophore and an acceptor fluorophore, a donor fluorophore binding specifically to a certain substance, an acceptor fluorophore binding specifically to the certain substance, and energy transfer between the donor fluorophore and the acceptor fluorophore occurring when both of the donor fluorophore and the acceptor fluorophore bind to the certain substance;

measuring a lifetime of fluorescence from acceptor fluorophores to determine a first timing, at which intensity of fluorescence from the acceptor fluorophores attenuates below a predetermined threshold after irradiation of excitation light;

measuring a lifetime of fluorescence from donor fluorophores to determine a second timing, at which intensity of fluorescence from the donor fluorophores attenuates below a second predetermined threshold after irradiation of excitation light, the fluorescence lifetime of the donor fluorophores being longer than the fluorescence lifetime of the acceptor fluorophores;

measuring a lifetime of fluorescence from the acceptor fluorophores and the donor fluorophores under energy-transfer condition to determine a third timing, at which intensity of fluorescence from the donor and acceptor fluorophores attenuates below a third predetermined threshold after irradiation of excitation light;

determining a first time period between the first timing and the third timing and a second time period between the third timing and the second timing;

preparing a control sample including only the donor fluorophores and the acceptor fluorophores;

irradiating, with excitation light, the control sample so that the donor fluorophores and the acceptor fluorophores emit fluorescence, measuring an intensity of the fluorescence emitted from the control sample in a first wavelength region and a second wavelength region during the first time period, to thereby obtain an intensity $I_{D1}$ of the first wavelength region and intensity $I_{A1}$ of the second wavelength region, the first wavelength region being set only within the fluorescence wavelength band of the donor fluorophores, the second wavelength region being set not only within the fluorescence wavelength band of the acceptor fluorophores but also within a predetermined amount of a part of the fluorescence wavelength band of the donor fluorophores;

measuring an intensity of the fluorescence emitted from the control sample in the first wavelength region and the second wavelength region during the second time period, to thereby obtain an intensity $I_{D2}$ of the first wavelength region and an intensity $I_{A2}$ of the second wavelength region;

determining energy transfer test information Z based on a ratio between the amounts $I_{D2}$ and $I_{D1}$ and a ratio between the amounts $I_{A2}$ and $I_{A1}$;

preparing a sample through adding the donor fluorophores and the acceptor fluorophores to the test sample, a part of the donor fluorophores and the acceptor fluorophores being under energy transfer condition if the certain substance exists in the test sample;

irradiating, with excitation light, the sample so that the donor fluorophores and the acceptor fluorophores emit fluorescence;

measuring an intensity of the fluorescence emitted from the sample in the first wavelength region and the second wavelength region during the first time period, to thereby obtain an intensity $I_{D1}'$ of the first wavelength region and an intensity $I_{A1}'$ of the second wavelength region;

measuring an intensity of the fluorescence emitted from the sample in the first wavelength region and the second wavelength region during the second time period, to thereby obtain an intensity $I_{D2}'$ of the first wavelength region and an intensity $I_{A2}'$ of the second wavelength region;

determining energy transfer information Z' based on a ratio between the amounts $I_{D2}'$ and $I_{D1}'$ and a ratio between the amounts $I_{A2}'$ and $I_{A1}'$; and determining, based on the energy transfer test information Z and the energy transfer information Z', information on the substance in the test sample.

25. The method as claimed in claim 24, wherein the ratio between the amounts $I_{D2}$ and $I_{D1}$ indicates an attenuation rate of the intensity of the first light from the control sample, and the ratio between the amounts $I_{A2}$ and $I_{A1}$ indicates an attenuation rate of the intensity of the second light from the control sample, the energy transfer test information Z being represented by a predetermined relationship between the ratio between the amounts $I_{D2}$ and $I_{D1}$ and the ratio between the amounts $I_{A2}$ and $I_{A1}$, and wherein the ratio between the amounts $I_{D2}'$ and $I_{D1}'$ indicates an attenuation rate of the intensity of the first light from the sample, and the ratio between the amounts $I_{A2}'$ and $I_{A1}'$ indicates an attenuation rate of the intensity of the second light from the sample, the energy transfer information Z' being represented by a predetermined relationship between the ratio between the amounts $I_{D2}'$ and $I_{D1}'$ and the ratio between the amounts $I_{A2}'$ and $I_{A1}'$.

26. The method as claimed in claim 25, wherein the predetermined relationship between the ratio between the amounts $I_{D2}$ and $I_{D1}$ and the ratio between the amounts $I_{A2}$ and $I_{A1}$ is represented by the following formula:

$$\{(I_{D2}/I_{D1})-(I_{A2}/I_{A1})\}/(I_{D2}/I_{D1}),$$

and wherein the predetermined relationship between the ratio between the amounts $I_{D2}'$ and $I_{D1}'$ and the ratio between the amounts $I_{A2}'$ and $I_{A1}'$ is represented by the following formula:

$$\{(I_{D2}'/I_{D1}')-(I_{A2}'/I_{A1}')\}/(I_{D2}'/I_{D1}').$$

* * * * *